(12) United States Patent
Witters et al.

(10) Patent No.: US 12,071,665 B2
(45) Date of Patent: Aug. 27, 2024

(54) NUCLEIC ACID CIRCULARIZATION AND AMPLIFICATION ON A SURFACE

(71) Applicant: Singular Genomics Systems, Inc., San Diego, CA (US)

(72) Inventors: Daan Witters, San Diego, CA (US); Eli N. Glezer, Del Mar, CA (US); Andrew King, San Diego, CA (US); Sabrina Shore, San Diego, CA (US); Ryan Shultzaberger, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/176,616

(22) Filed: Mar. 1, 2023

(65) Prior Publication Data

US 2023/0357843 A1    Nov. 9, 2023

Related U.S. Application Data

(63) Continuation of application No. PCT/US2021/056349, filed on Oct. 22, 2021.

(60) Provisional application No. 63/104,363, filed on Oct. 22, 2020.

(51) Int. Cl.
*C12Q 1/68* (2018.01)
*C12Q 1/6874* (2018.01)

(52) U.S. Cl.
CPC ................... *C12Q 1/6874* (2013.01)

(58) Field of Classification Search
CPC ............... C12Q 1/6834; C12Q 1/6869
See application file for complete search history.

(56) References Cited

U.S. PATENT DOCUMENTS

| | | | |
|---|---|---|---|
| 4,318,846 A | 3/1982 | Khanna et al. | |
| 5,034,506 A | 7/1991 | Summerton et al. | |
| 5,066,580 A | 11/1991 | Lee | |
| 5,188,934 A | 2/1993 | Menchen et al. | |
| 5,235,033 A | 8/1993 | Summerton et al. | |
| 5,366,860 A | 11/1994 | Bergot et al. | |
| 5,599,675 A | 2/1997 | Brenner | |
| 5,641,658 A | 6/1997 | Adams et al. | |
| 5,688,648 A | 11/1997 | Mathies et al. | |
| 5,750,341 A | 5/1998 | Macevicz | |
| 5,763,594 A | 6/1998 | Hiatt et al. | |
| 5,800,996 A | 9/1998 | Lee et al. | |
| 5,808,045 A | 9/1998 | Hiatt et al. | |
| 5,847,162 A | 12/1998 | Lee et al. | |
| 5,872,244 A | 2/1999 | Hiatt et al. | |
| 6,210,891 B1 | 4/2001 | Nyren et al. | |
| 6,232,465 B1 | 5/2001 | Hiatt et al. | |
| 6,274,320 B1 | 8/2001 | Rothberg et al. | |
| 7,057,026 B2 | 6/2006 | Barnes et al. | |
| 7,115,400 B1 | 10/2006 | Adessi et al. | |
| 7,541,444 B2 | 6/2009 | Milton et al. | |
| 7,790,418 B2 | 9/2010 | Mayer | |
| 10,738,072 B1 | 8/2020 | Graham et al. | |
| 11,608,528 B2* | 3/2023 | Patterson ............ | C12Q 1/6837 |
| 2002/0146745 A1 | 10/2002 | Natan et al. | |
| 2008/0009420 A1 | 1/2008 | Schroth et al. | |
| 2009/0117573 A1* | 5/2009 | Fu ..................... | C12Q 1/6858 435/6.14 |
| 2011/0269631 A1* | 11/2011 | Fu ..................... | C12Q 1/6858 506/7 |
| 2012/0208705 A1 | 8/2012 | Steemers et al. | |
| 2012/0208724 A1 | 8/2012 | Steemers et al. | |
| 2012/0309650 A1 | 12/2012 | Patel et al. | |
| 2013/0012399 A1 | 1/2013 | Myers et al. | |
| 2014/0322759 A1 | 10/2014 | Skirgaila et al. | |
| 2016/0304954 A1 | 10/2016 | Lin et al. | |
| 2018/0258472 A1 | 9/2018 | Glezer | |
| 2018/0274024 A1 | 9/2018 | Ju et al. | |
| 2018/0371006 A1 | 12/2018 | Kazakov et al. | |
| 2020/0181692 A1 | 6/2020 | Oberstrass | |
| 2022/0349002 A1* | 11/2022 | Patterson ............ | C12Q 1/6837 |

FOREIGN PATENT DOCUMENTS

| | | |
|---|---|---|
| WO | WO-1989/010977 A1 | 11/1989 |
| WO | WO-1996/007669 A1 | 3/1996 |
| WO | WO-2004/018497 A2 | 3/2004 |
| WO | WO-2012/061832 A1 | 5/2012 |
| WO | WO-2017/205336 A1 | 11/2017 |
| WO | WO-2018/148723 A1 | 8/2018 |
| WO | WO-2020/056044 A1 | 3/2020 |

OTHER PUBLICATIONS

Bains, W. et al. (1988). "A novel method for nucleic acid sequence determination," *Journal of theoretical biology* 135(3): 303-307.
Beattie, W.G. et al. (1995). "Hybridization of DNA targets to glass-tethered oligonucleotide probes," *Mol Biotechnol* 4:213-225.
Bentley, D. R. et al. (2008). "Accurate whole human genome sequencing using reversible terminator chemistry," *Nature* 456(7218): 53-59.
Bergen K. et al. (2013). "Structures of KOD and 9° N DNA polymerases complexed with primer template duplex," Chembiochem 14(9):1058-1062.
Drmanac, S. et al. (1998). "Accurate sequencing by hybridization for DNA diagnostics and individual genomics," *Nature biotechnology* 16(1): 54-58.
Fodor, S. et al. (1991). "Light-Directed, Spatially Addressable Parallel Chemical Synthesis," *Science* 251:767-773.
Fuller, C.W. et al. (2016) "Real-time single-molecule electronic DNA sequencing by synthesis using polymer-tagged nucleotides on a nanopore array," *PNAS* 133(19):5233-5238.

(Continued)

*Primary Examiner* — Kenneth R Horlick

(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are compositions and methods for amplification of nucleic acid templates, including hybridizing a linear polynucleotide to an immobilized primer on a surface, circularizing the linear polynucleotide to form a circular polynucleotide, and extending the primer with a polymerase.

23 Claims, 8 Drawing Sheets

Specification includes a Sequence Listing.

(56) References Cited

OTHER PUBLICATIONS

Guo, J. et al. (2008). "Four-color DNA sequencing with 3'-O-modified nucleotide reversible terminators and chemically cleavable fluorescent dideoxynucleotides," *Proceedings of the National Academy of Sciences* 105(27): 9145-9150.

International Search Report and Written Opinion mailed on Jan. 31, 2022, for PCT application PCT/US2021/056349, filed Oct. 22, 2021, 11 pages.

Kringel, D. et al. (2018, e-published Sep. 19, 2018) "Development of an AmpliSeqTM Panel for Next-Generation Sequencing of a Set of Genetic Predictors of Persisting Pain," *PubMed Central: Front Pharmacol.* 9:1008.

Kumar, S. et al. (2012) "PEG-Labeled Nucleotides and Nanopore Detection for Single Molecule DNA Sequencing by Synthesis," *Scientific Reports* 2(684):1-7.

Lage, J. M. et al. (2003). "Whole genome analysis of genetic alterations in small DNA samples using hyperbranched strand displacement amplification and array-CGH," *Genome research* 13(2): 294-307.

Lizardi, P. et al. (1998). "Mutation detection and single-molecule counting using isothermal rolling-circle amplification," *Nature Genetics* 19: 225-232.

Nilsson, M. et al. (1994). "Padlock Probes: Circularizing Oligonucleotides for Localized DNA Detection," *Science* 265: 2085-2088.

Rehm H.L. (2013, e-published Mar. 12, 2013) "Disease-targeted sequencing: a cornerstone in the clinic," *Nat Rev Genet* 14(4):295-300.

Ronaghi, M. et al. (1998). "A sequencing method based on real-time pyrophosphate," *Science* 281(5375): 363-365.

Ronaghi, M. et al. (1996). "Real-time DNA sequencing using detection of pyrophosphate release," *Anal Biochem* 242(1):84-9.

Ronaghi, M. (2001). "Pyrosequencing sheds light on DNA sequencing," *Genome research* 11(1): 3-11.

Shendure, J. et al. (2005). "Accurate multiplex polony sequencing of an evolved bacterial genome," *Science* 309(5741): 1728-1732.

Simen, B. et al. (2015). "Validation of a Next-Generation-Sequencing Cancer Panel for Use in the Clinical Laboratory," *Arch Pathol Lab Med* 139(4):508-517.

Singh, R.R .et al. (2013) "Clinical Validation of a Next-Generation Sequencing Screen for Mutational Hotspots in 46 Cancer-Related Genes," *The Journal of Molecular Diagnostics* 15(5):607-622.

Southworth, M. W. et al. (1996). "Cloning of thermostable DNA polymerases from hyperthermophilic marine Archaea with emphasis on *Thermococcus* sp. 9 degrees N-7 and mutations affecting 3'-5' exonuclease activity," *PNAS* 93(11): 5281-5285.

Yohe, S. et al. (2015). "Clinical validation of targeted next-generation sequencing for inherited disorders," *Archives of Pathology and Laboratory Medicine* 139(2):204-210.

\* cited by examiner

P1

P2

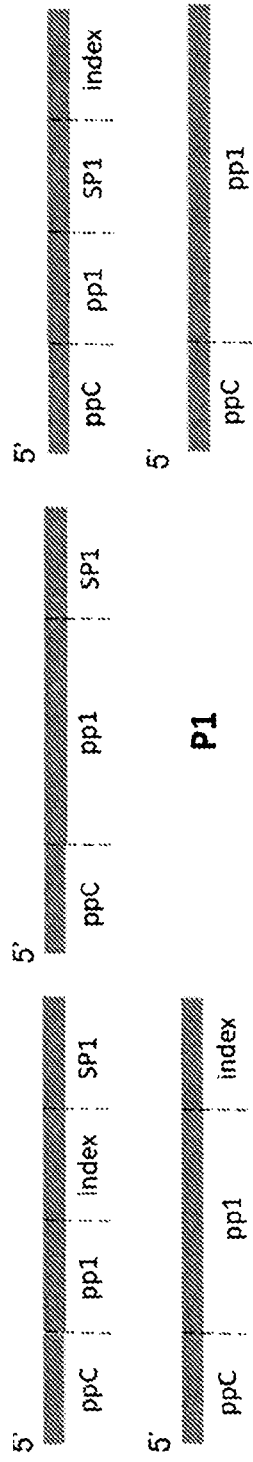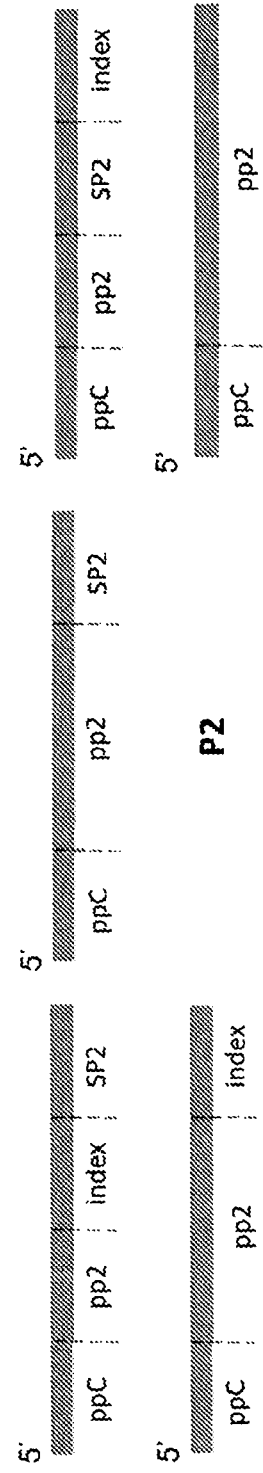
FIG. 2C
FIG. 2D

NUCLEIC ACID CIRCULARIZATION AND AMPLIFICATION ON A SURFACE

CROSS-REFERENCES TO RELATED APPLICATIONS

This application is a continuation of PCT Application PCT/US2021/056349, filed Oct. 22, 2021, which claims the benefit of U.S. Provisional Application No. 63/104,363, filed Oct. 22, 2020, each of which are incorporated herein by reference in their entirety and for all purposes.

SEQUENCE LISTING

The instant application contains a Sequence Listing which has been submitted electronically in ST.26 format and is hereby incorporated by reference in its entirety. Said Sequence Listing, created on Feb. 24, 2023, is named 051385-536C01US SEQUENCE LISTING ST26.xml and is 12,028 bytes in size.

BACKGROUND

Nucleic acid amplification is an indispensable technique used in medical laboratory and clinical laboratory research for a broad variety of applications. A majority of nucleic acid amplification (e.g., DNA amplification) is performed using polymerase chain reaction (PCR), though in the past decade alternative amplification methods have emerged that eliminate thermal and/or chemical cycling. Rolling circle amplification (RCA) is an efficient isothermal enzymatic process that generates long single-stranded nucleic acid sequences. In RCA, a strand-displacing polymerase (e.g., Phi29) continuously extends a primer hybridized to a circular template by adding nucleotides at a constant temperature (e.g., 37° C.). As the initial template molecule in RCA is circular, the displacement activity of the polymerase enables continued amplification of the template into a single, linear molecule containing tandem repeats of the starting template (referred to as a concatemer). This displacement can in theory continue infinitely, although there are practical limits to amplification.

Most next generation sequencing (NGS) library prep methods are based on the modification and amplification of linear DNA molecules. To convert a linear nucleic acid to circular library, additional steps are required which typically increase library prep time and overall user burden.

BRIEF SUMMARY

In view of the foregoing, innovative approaches to address issues with existing sequencing technologies are needed. Disclosed herein are solutions to these and other problems in the art which, in embodiments, increase the signal intensity and accuracy of high throughput sequencing methods. In certain embodiments, the compositions and methods provided herein reduce the number of steps required to implement amplification of a nucleic acid template in NGS, reducing product loss, and eliminating burdensome purification steps and exonuclease treatment.

In an aspect is provided a method of sequencing a linear template polynucleotide, the method including: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; and (d) sequencing the first extension product or a complement thereof by extending a sequencing primer hybridized thereto. In embodiments, the method further includes hybridizing the first extension product to one or more surface-immobilized oligonucleotides immobilized on the surface, prior to or concurrent with the sequencing.

In an aspect is provided a method of sequencing a linear template polynucleotide, the method including: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) extending the splint primer with a strand-displacing polymerase, wherein the extension generates a first extension product including one or more complements of the circular template polynucleotide; and (d) sequencing the first extension product or a complement thereof by extending a sequencing primer hybridized thereto. In embodiments, the method further includes hybridizing the first extension product to one or more surface-immobilized oligonucleotides immobilized on the surface, prior to or concurrent with the sequencing.

In an aspect is provided a method of detecting a linear template polynucleotide, the method including: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; and (d) detecting the first extension product or a complement thereof. In embodiments, detecting includes sequencing. In embodiments, detecting includes annealing a sequencing primer to the extension product or complement thereof and extending the sequencing primer to incorporate a detectable label that indicates the identity of a nucleotide in the extension product or complement thereof, and detecting the detectable label, and optionally repeating the extending and detecting steps. In embodiments, detecting includes hybridizing a nucleic acid stain (e.g., an oligonucleotide including a label, such as a FAM-labeled oligonucleotide) and measuring the emission of the stain following excitation. In embodiments, the method further includes hybridizing the first extension product to one or more surface-immobilized oligonucleotides immobilized on the surface, prior to, or concurrent with the detecting.

In an aspect is provided a method of detecting a linear template polynucleotide, the method including: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) extending the splint primer with a strand-displacing polymerase, wherein the extension generates a first extension product including one or more complements of the circular template polynucleotide; and (d) detecting the first extension product or a complement thereof. In embodiments, detecting includes sequencing. In embodiments, detecting includes annealing a sequencing primer to the extension product or complement thereof and extending the sequencing primer to incorporate a detectable label that indicates the identity of a nucleotide in the extension product or complement thereof, and detecting the detectable label, and optionally repeating the extending and detecting steps. In embodiments, detecting includes hybridizing a nucleic acid stain (e.g., an oligonucleotide including a label, such as a FAM-labeled oligonucleotide) and measuring the emission of the stain following excitation. In embodiments, the method further includes hybridizing the first extension product to one or more surface-immobilized oligonucleotides immobilized on the surface, prior to, or concurrent with the detecting.

In an aspect is provided herein a method of selectively sequencing a linear template polynucleotide, the method including (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) hybridizing a probe oligonucleotide to the circular template polynucleotide from step (b); (d) separating the probe-hybridized circular template polynucleotide from template polynucleotides not hybridized to a probe; and (e) sequencing the probe-hybridized template polynucleotide of step (d).

In an aspect is provided herein a method of selectively sequencing a linear template polynucleotide, the method including (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; (d) hybridizing a probe oligonucleotide to the first extension product from step (c); (e) separating the probe-hybridized extension product from extension products not hybridized to a probe; and (f) sequencing the probe-hybridized extension product of step (e).

In an aspect is provided herein a method of selectively sequencing a linear template polynucleotide, the method including (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) extending the splint primer with a strand-displacing polymerase, wherein the extension generates a first extension product including one or more complements of the circular template polynucleotide; (d) hybridizing a probe oligonucleotide to the first extension product from step (c); (e) separating the probe-hybridized extension product from extension products not hybridized to a probe; and (f) sequencing the probe-hybridized extension product of step (e).

In an aspect is provided a substrate including: (a) a splint primer immobilized on the substrate via a first linker; (b) a plurality of surface-immobilized oligonucleotides immobilized to the substrate via a second linker; and (c) a linear template polynucleotide hybridized to the splint primer; wherein (i) the splint primer includes, in the 5' to 3' direction, a first sequence and a second sequence, (ii) the first sequence is complementary to a 5' portion of the linear template polynucleotide, (iii) the second sequence is complementary to a 3' portion of the linear template polynucleotide, and (iv) the plurality of surface-immobilized oligonucleotides are hybridizable to a complement of the linear template polynucleotide.

BRIEF DESCRIPTION OF THE DRAWINGS

FIG. 1A. A double-stranded template is prepared according to standard library prep methods (e.g., fragmenting, polishing, A-tailing, etc.) and is optionally phosphorylated on the 5' ends. Adapters P1 and P2', or alternatively P1' and P2 are ligated to the ends of the template. FIG. 1B. Circularization of target DNA is achieved using surface-immobilized primer oligo sequence (also referred to herein as a "splint primer") that has complementarity to common 5' and 3' adapter sequences (further described herein and in FIGS. 2A-2D) in a sequencing library. FIG. 1C. Once circularized, the constructs can be amplified by rolling circle amplification (RCA) by extending directly from the splint primer oligo. FIG. 1D shows one example of a single-stranded DNA template wherein the P1 and P2' adapters ligated to the ends. The P1 adapter includes a platform priming capture sequence (ppC). FIG. 1E shows the circularization of target DNA using surface-immobilized splint primer oligo sequence that includes a complementary region to the platform priming capture sequence, ppC', as well as a platform primer sequence, pp2, which is further described herein. FIG. 1E depicts the capture of a target nucleic acid of FIG. 1D and subsequent ligation to form a circular template. Once circularized, the constructs can be amplified by rolling circle amplification (RCA) by extending directly from the splint primer oligo, depicted in FIG. 1F. A second primer (exponential amplification primer) can be included on the surface to facilitate exponential amplification of the template. The 5' end of any of the surface immobilized linkers may be covalently attached to a solid surface via an optional linker.

FIGS. 2A-2D. Schematic of the oligo sequences used in some embodiments. FIGS. 2A-2B show examples of the oligo sequences, P1 and P2, which contain a platform primer 1 (pp1) and platform primer 2 (pp2), respectively, which is a sequence complementary to a surface-immobilized oligo, an optional index sequence (i) for multiplexing samples, and a region complementary to a sequencing primer (SP). In embodiments, the P1 adapter consists of (pp1)-(i)-(SP1) and a P2' adapter consists of (pp2')-(i)-(SP2'). The index sequence in P1 may be the same or different to the index sequence in P2. To enable exponential amplification of RCA product, the platform primer sequence may further include a sequence that is complementary to a splint primer and an exponential amplification primer, or the complement thereof. The dashed lines are indicative of regions within the adapter and are included to aid the eye in the different arrangement of the sequences and are not indicative of the overall size/length (i.e., the index sequence may not be the same length as the sequencing primer despite the illustration showing the index sequence and sequencing primer as being the same size). FIG. 2C and FIG. 2D depict examples of P1 and P2 adapters further including a ppC sequence. It is understood that any P1 adapter shown in FIG. 2A or FIG. 2C, or the complement thereof, may be combined with any P2 adapter shown in FIG. 2B or FIG. 2D, or complement thereof, when preparing the template nucleic acid sequence. The 5' end of any of the P1 or P2 adapters may be covalently attached to a solid surface via a linker, not shown.

FIG. 4A shows clusters form, as indicated by the punctate points, in the presence of the combination of both pp1 and pp1', for example see the top leftmost and middle image of FIG. 4A. When the platform primer sequences, pp1 or pp1', are absent from P1 or P2 no amplification product is observed, see the bottom leftmost and middle image of FIG. 4A. FIG. 4B depicts an experiment that varied the length of platform specific primer sequences pp1 or pp1': 20 nt, 15 nt, or 10 nt. For these experiments, a complex library was used (fragments of the S. Typhimurium genome). Clusters were stained with FAM-labeled probes. While clusters formed in all conditions tested, as presented in FIG. 4B, the low and medium range length (10 nt and 15 nt) primers resulted in significantly more sequenceable clusters compared to the longer length (20 nt) primers.

DETAILED DESCRIPTION

I. Definitions

Figure 1A:
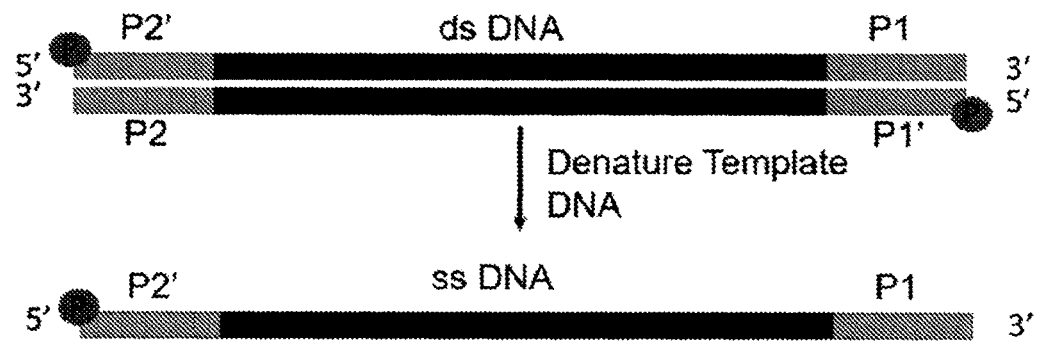
FIGS. 1A-1F. Schematic of on-surface circularization and amplification of a DNA template for sequencing.

All patents, patent applications, articles and publications mentioned herein, both supra and infra, are hereby expressly incorporated herein by reference in their entireties.

The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances, two or more associated species are "tethered", "coated", "attached", or "immobilized" to one another or to a common solid or semisolid support. An association may refer to covalent or non-covalent means for attaching labels to solid or semi-solid supports such as beads. In embodiments, primers on or bound to a solid support are covalently attached to the solid support. An association may comprise hybridization between a target and a label.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme.

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis. A "splint primer" is used according to its plain and ordinary meaning and refers to a primer having 2 or more sequences complementary to two or more portions of a template polynucleotide. In embodiments, the two sequences are adapter sequences wherein one adapter sequences binds (i.e., hybridizes) to a 5' portion of the template polynucleotide and the other adapter binds (i.e., hybridizes) to a 3' portion of the template polynucleotide.

As used herein, the terms "solid support" and "substrate" and "solid surface" refers to discrete solid or semi-solid surfaces (e.g. discrete solid or semi-solid material or group of materials having one or more surfaces), to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports in the form of discrete particles may be referred to herein as "beads," which alone does not imply or require any particular shape. A bead can be non-spherical in shape. A solid support may further comprise a polymer or hydrogel on the surface to which the primers are attached (e.g., the splint primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008).

In some embodiments, a nucleic acid comprises a capture nucleic acid. A capture nucleic acid refers to a nucleic acid that is attached to a substrate (e.g., covalently attached). In some embodiments, a capture nucleic acid comprises a primer. In some embodiments, a capture nucleic acid is a nucleic acid configured to specifically hybridize to a portion of one or more nucleic acid templates (e.g., a template of a library). In some embodiments a capture nucleic acid configured to specifically hybridize to a portion of one or more nucleic acid templates is substantially complementary to a suitable portion of a nucleic acid template, or an amplicon thereof. In some embodiments a capture nucleic acid is configured to specifically hybridize to a portion of an adapter, or a portion thereof. In some embodiments a capture nucleic acid, or portion thereof, is substantially complementary to a portion of an adapter, or a complement thereof. In embodiments, a capture nucleic acid is a probe oligonucleotide. Typically, a probe oligonucleotide is complementary to a target polynucleotide or portion thereof, and further comprises a label (such as a binding moiety) or is attached to a surface, such that hybridization to the probe oligonucleotide permits the selective isolation of probe-bound polynucleotides from unbound polynucleotides in a population. A probe oligonucleotide may or may not also be used as a primer.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

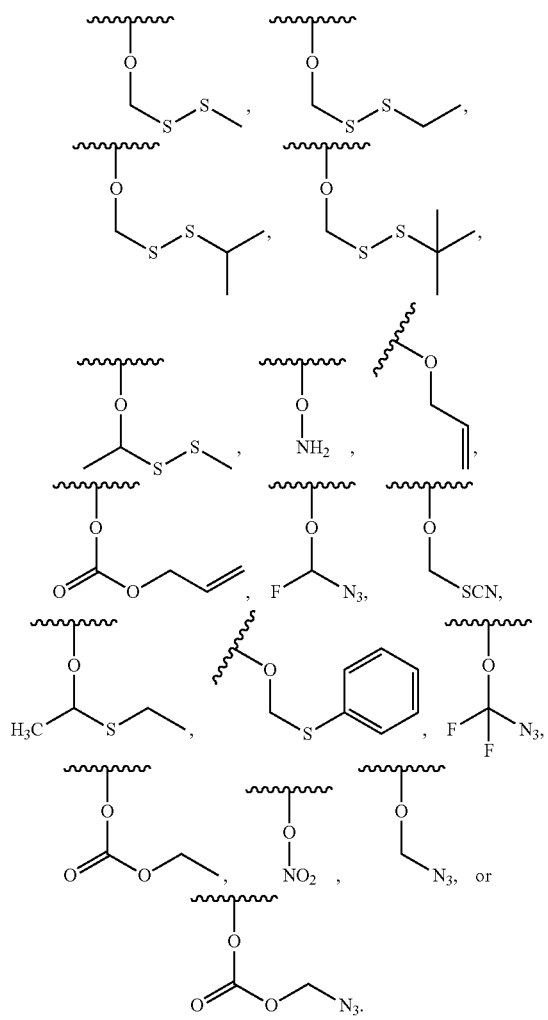

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site blast.ncbi.nlm.nih.gov/Blast.cgi or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator.

As used herein, the term "barcode" or "index" or "unique molecular identifier (UMI)" refers to a known nucleic acid sequence that allows some feature with which the barcode is associated to be identified. Typically, a barcode is unique to a particular feature in a pool of barcodes that differ from one another in sequence, and each of which is associated with a different feature. In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are 10-50 nucleotides in length, such as 15-40 or 20-30 nucleotides in length. In a pool of different barcodes, barcodes may have the same or different lengths. In general, barcodes are of sufficient length and comprise sequences that are sufficiently different to allow the identification of associated features (e.g., a binding moiety or analyte) based on barcodes with which they are associated. In embodiments, a barcode can be identified accurately after the mutation, insertion, or deletion of one or more nucleotides in the barcode sequence, such as the mutation, insertion, or deletion of 1, 2, 3, 4, 5, or more nucleotides. In embodiments, each barcode in a plurality of barcodes differs from every other barcode in the plurality by at least three nucleotide positions, such as at least 3, 4, 5, 6, 7, 8, 9, 10, or more nucleotide positions.

In some embodiments, a nucleic acid comprises a label. As used herein, the term "label" or "labels" are used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyperbranched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "sequencing reaction mixture" is used in accordance with its plain and ordinary meaning and refers to an aqueous mixture that contains the reagents necessary to allow a nucleotide or nucleotide analogue to be added to a DNA strand by a DNA polymerase.

As used herein, the term "extension" or "elongation" is used in accordance with their plain and ordinary meanings and refer to synthesis by a polymerase of a new polynucleotide strand complementary to a template strand by adding free nucleotides from a reaction mixture that are complementary to the template in a 5'-to-3' direction, including condensing a 5'-phosphate group of a dNTPs with a 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a primer or capture nucleic acid to a portion of a target nucleic acid (e.g., a template, or adapter portion of a template) that is substantially complementary to the primer or capture nucleic acid. The terms "hybridize" and "anneal", and grammatical variations thereof, are used interchangeably herein. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

A nucleic acid can be amplified by a thermocycling method or by an isothermal amplification method. In some embodiments, a rolling circle amplification method is used. In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is a substrate including (a) a splint primer immobilized on the substrate via a first linker; (b) a plurality of surface-immobilized oligonucleotides immobilized to the substrate via a second linker; and (c) a linear template polynucleotide hybridized to the splint primer; wherein (i) the splint primer includes, in the 5' to 3' direction, a first sequence and a second sequence, (ii) the first sequence is complementary to a 5' portion of the linear template polynucleotide, (iii) the second sequence is complementary to a 3' portion of the linear template polynucleotide, and (iv) the plurality of surface-immobilized oligonucleotides are hybridizable to a complement of the linear template polynucleotide. In embodiments, the substrate includes a polymer or hydrogel on the substrate surface to which the primers are attached (e.g., the splint primers are covalently attached to the polymer, wherein the polymer is in direct contact with the substrate).

In embodiments, the linear template polynucleotide includes a first adapter polynucleotide joined to a 5' end of a sample polynucleotide, and a second adapter polynucleotide joined to a 3' end of the sample polynucleotide, wherein (i) the first adapter polynucleotide includes a portion that is hybridized to the first sequence of the splint primer, and (ii) the second adapter polynucleotide includes a portion that is hybridized to the second sequence of the splint primer.

In embodiments, one or both of the first adapter polynucleotide and the second adapter polynucleotide include a portion that is not hybridized to the splint primer, wherein the portion that is hybridized to the splint primer is distal to the portion that is not hybridized to the splint primer. In embodiments, both of the first adapter polynucleotide and the second adapter polynucleotide include a portion that is not hybridized to the splint primer, wherein the portion that is hybridized to the splint primer is distal to the portion that is not hybridized to the splint primer. In embodiments, the first adapter polynucleotide includes a portion that is not hybridized to the splint primer, wherein the portion that is hybridized to the splint primer is distal to the portion that is not hybridized to the splint primer. In embodiments, the second adapter polynucleotide includes a portion that is not hybridized to the splint primer, wherein the portion that is hybridized to the splint primer is distal to the portion that is not hybridized to the splint primer.

In embodiments, the portion that is not hybridized to the splint primer includes an index sequence. In embodiments, the index sequence is about or at least about 5, 6, 7, 8, 9, 10, 15, 20, 25, 30, 40, 50, 75 or more nucleotides in length. In embodiments, the index sequence is shorter than 20, 15, 10, 9, 8, 7, 6, or 5 nucleotides in length. In embodiments, the index sequence is 10-50 nucleotides in length, such as 15-40 or 20-30 nucleotides in length.

In embodiments, the plurality of surface-immobilized oligonucleotides are hybridizable to a complement of (a) the portion of the first adapter polynucleotide that is hybridized to the first sequence of the splint primer; or (b) the portion of the second adapter polynucleotide that is hybridized to the second sequence of the splint primer.

In embodiments, the plurality of surface-immobilized oligonucleotides are hybridizable to a complement of (a) the portion of the first adapter polynucleotide that is not hybridized to the splint primer; or (b) the portion of the second adapter polynucleotide that is not hybridized to the splint primer.

In embodiments, the plurality of surface-immobilized oligonucleotides include blocking groups at their 3' ends that prevent polymerase extension. Non-limiting examples of 3' blocking groups include a 3'-$ONH_2$ blocking group, a 3'-O-allyl blocking group, or a 3'-O-azidomethyl blocking group.

In embodiments, the splint primer is about 5 to about 25 nucleotides in length. In embodiments, the splint primer is about 10 to about 40 nucleotides in length. In embodiments, the splint primer is about 5 to about 100 nucleotides in length. In embodiments, the splint primer is about 20 to 200 nucleotides in length. In embodiments, the splint primer is about or at least about 5, 6, 7, 8, 9, 10, 12, 15, 18, 20, 25, 30, 35, 40, 50 or more nucleotides in length. In embodiments, the splint primer is about or at least about 10 nucleotides in length. In embodiments, the splint primer is about or at least about 15 nucleotides in length. In embodiments, the splint primer is about or at least about 25 nucleotides in length.

In embodiments, the linear template polynucleotide is about 100 to about 1000 nucleotides in length. In embodiments, the linear template polynucleotide is about 1000 to about 2000 nucleotides in length. In embodiments, the linear template polynucleotide is about 2000 to about 3000 nucleotides in length. In embodiments, the linear template polynucleotide is about 3000 to about 4000 nucleotides in length. In embodiments the linear template polynucleotide is about 4000 to about 5000 nucleotides in length. In embodiments, the linear template polynucleotide is about 100 to about 300 nucleotides in length. In embodiments, the linear template polynucleotide is about 300 to about 500 nucleotides in length. In embodiments, the linear template polynucleotide is about 500 to about 1000 nucleotides in length. In embodiments, the linear template polynucleotide is about 300 to about 600 nucleotides in length.

In embodiments, the linear template polynucleotide includes a genomic sequence of interest. In embodiments, the linear template polynucleotide includes one or more genomic sequences of interest. In embodiments, the linear template polynucleotide includes more than one genomic sequence of interest. In embodiments, the linear template polynucleotide includes cfDNA.

In embodiments, the composition further includes an additive that lowers a DNA denaturation temperature. In embodiments, the composition includes an additive such as betaine, dimethyl sulfoxide (DMSO), ethylene glycol, formamide, glycerol, guanidine thiocyanate, 4-methylmorpholine 4-oxide (NMO), or a mixture thereof.

In embodiments, the composition further includes a denaturant. The denaturant may be acetic acid, hydrochloric acid, nitric acid, formamide, guanidine, sodium salicylate, sodium hydroxide, dimethyl sulfoxide (DMSO), propylene glycol, urea, or a mixture thereof.

In embodiments, the splint primer and the surface-immobilized oligonucleotides are covalently attached to the solid support. In embodiments, the 5' end of the splint primer contains a functional group that is tethered to the solid support. Non-limiting examples of covalent attachment include amine-modified polynucleotides reacting with epoxy or isothiocyanate groups on the solid support, succinylated polynucleotides reacting with aminophenyl or aminopropyl functional groups on the solid support, dibenzocycloctyne-modified polynucleotides reacting with azide functional groups on the solid support (or vice versa), trans-cyclooctyne-modified polynucleotides reacting with tetrazine or methyl tetrazine groups on the solid support (or vice versa), disulfide modified polynucleotides reacting with mercapto-functional groups on the solid support, amine-functionalized polynucleotides reacting with carboxylic acid groups on the core via 1-ethyl-3-(3-dimethylaminopropyl)-carbodiimide hydrochloride (EDC) chemistry, thiol-modified polynucleotides attaching to a solid support via a disulphide bond or maleimide linkage, alkyne-modified polynucleotides attaching to a solid support via copper-catalyzed click reactions to azide functional groups on the solid support, and acrydite-modified polynucleotides polymerizing with free acrylic acid monomers on the solid support to form polyacrylamide or reacting with thiol groups on the solid support. In embodiments, the splint primer is attached to the solid support polymer through electrostatic binding. For example, the negatively charged phosphate backbone of the primer may be bound electrostatically to positively charged monomers in the solid support.

In embodiments, the substrate is glass or quartz, such as a microscope slide, having a surface that is uniformly silanized. This may be accomplished using conventional protocols e.g., Beattie et a (1995), Molecular Biotechnology, 4: 213. Such a surface is readily treated to permit end-attachment of oligonucleotides (e.g., forward and reverse primers, and/or a splint primer) prior to amplification. In embodiments the solid support surface further includes a polymer coating, which contains functional groups capable of immobilizing primers. In some embodiments, the solid support includes a patterned surface suitable for immobilization of primers in an ordered pattern. A patterned surface refers to an arrangement of different regions in or on an exposed layer of a solid support. For example, one or more of the regions can be features where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the primers are randomly distributed upon the solid support. In some embodiments, the primers are distributed on a patterned surface. In embodiments, the substrate is a particle.

In embodiments, the splint primer is immobilized on the substrate via a first linker and the surface-immobilized oligonucleotides are immobilized to the substrate via a second linker. In embodiments, the linker, the splint primer, or the surface-immobilized oligonucleotides include one or more cleavable sites. A cleavable site is a site which allows controlled cleavage of the immobilized oligonucleotide strand (e.g., the linker, the splint primer, or the surface-immobilized oligonucleotide) by chemical, enzymatic or photochemical means.

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the surface immobilized primer (e.g., within the polynucleotide sequence of the primer). In embodiments, the linker, the splint primer, or the surface-immobilized oligonucleotide includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, a cleavable site can include a nucleotide or nucleotide sequence that may be fragmented by various means. For example, a cleavable site may include a restriction endonuclease site; at least one ribonucleotide cleavable with an RNAse; nucleotide analogues cleavable in the presence of certain chemical agent(s); a diol linkage cleavable by treatment with periodate; a disulfide group cleavable with a chemical reducing agent; a cleavable moiety that may be subject to photochemical cleavage; and a peptide cleavable by a peptidase enzyme or other suitable means. See e.g., U.S. Pat. Publ. Nos. 2012/0208705 and 2012/0208724, and PCT Publ. No. WO 2012/061832, each of which is incorporated by reference in its entirety.

In embodiments, a plurality of substrates (e.g., particles) are immobilized on a solid support (e.g., a patterned flow cell or array). In embodiments, the plurality of substrates are bound to a discrete site on a solid support. In embodiments, each of the substrates are in a well of a multiwell container. In embodiments, each substrate includes a splint primer immobilized thereto.

In an aspect is provided an array (e.g., a solid support) of particles, wherein one or more particles on the array includes (a) a splint primer immobilized on the particle via a first linker; (b) a plurality of particle-immobilized oligonucleotides immobilized to the particle via a second linker; and (c) a linear template polynucleotide hybridized to the splint primer; wherein (i) the splint primer includes, in the 5' to 3' direction, a first sequence and a second sequence, (ii) the first sequence is complementary to a 5' portion of the linear template polynucleotide, (iii) the second sequence is complementary to a 3' portion of the linear template polynucleotide, and (iv) the plurality of particle-immobilized oligonucleotides are hybridizable (i.e., capable of hybridizing) to a complement of the linear template polynucleotide. In embodiments, the one or more particles includes a polymer or hydrogel on the particle surface to which the primers are attached (e.g., the splint primers are covalently attached to the polymer, wherein the polymer is in direct contact with the substrate).

In an aspect is a kit, wherein the kit includes the substrate as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase enzyme, Taq DNA Ligase, HiFi Taq DNA Ligase, T4 DNA ligase, or Ampligase® DNA Ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 DNA ligase, or Ampligase® DNA Ligase), and (b) ligation enzyme cofactors. In embodiments, the kit further includes instructions. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. The kits may include, e.g., any useful components (e.g., extension and/or amplification primers, substrates and/or composition, reaction buffers, etc.) described herein, in any desired combination. In embodiments, a kit of the present disclosure includes a first amplification primer that includes a 3' hybridization region and a 5' region including all or a portion of a first sequencing adapter. The kit further includes a second amplification primer that includes a 3' hybridization region and a 5' region including all or a portion of a second sequencing adapter. Components of the kits may be present in separate containers, or multiple components may be present in a single container. Kits may include DNA standards and other forms of positive and negative controls. Additionally, a kit may further include DNA quantification materials such as, for example, DNA binding dye such as SYBR™ green or SYBR™ gold (available from Thermo Fisher Scientific, Waltham, MA) or the alike for use with a Qubit™ fluorometer (e.g., available from Thermo Fisher Scientific, Waltham, MA), or PicoGreen™ dye (e.g., available from Thermo Fisher Scientific, Waltham, MA) for use on a suitable fluorescence spectrometer or a real-time PCR machine or digital-droplet PCR machine.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant $P.\ abyssi$ polymerase (e.g., such as a mutant $P.\ abyssi$ polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the kit includes nucleotides (i.e., dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate and/or modified nucleotides.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The kit may further include one or more other containers including PCR and sequencing buffers, diluents, subject sample extraction tools (e.g. syringes, swabs, etc.), and package inserts with instructions for use. In addition, a label can be provided on the container with directions for use, such as those described above; and/or the directions and/or other information can also be included on an insert which is included with the kit; and/or via a website address provided therein. The kit may also comprise laboratory tools such as, for example, sample tubes, plate sealers, microcentrifuge tube openers, labels, magnetic particle separator, foam inserts, ice packs, dry ice packs, insulation, etc. The kits may further include pre-packaged or application-specific functionalized substrates as described herein for use in amplification and/or detection of the library molecules. In embodiments, the substrate may include a surface suitable for performing sequencing reactions therein.

III. Methods of Amplifying and Sequencing

In an aspect is a method of sequencing a linear template polynucleotide. In embodiments, the method includes: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; and (d) sequencing the first extension product or a complement thereof by extending a sequencing primer hybridized thereto. In embodiments, the method further includes hybridizing the first extension product to one or more surface-immobilized oligonucleotides immobilized on the surface, prior to or concurrent with the sequencing.

In embodiments, the method includes: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; (d) hybridizing the first extension product to one or more surface-immobilized oligonucleotides immobilized on the surface; and (e) sequencing the first extension product or a complement thereof by extending a sequencing primer hybridized thereto.

In an aspect is provided a method of detecting a linear template polynucleotide, the method including: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; and (d) detecting the first extension product or a complement thereof. In embodiments, detecting includes sequencing. In embodiments, detecting includes annealing a sequencing primer to the extension product or complement thereof and extending the sequencing primer to incorporate a detectable label that indicates the identity of a nucleotide in the extension product or complement thereof, and detecting the detectable label, and optionally repeating the extending and detecting steps. In embodiments, detecting includes hybridizing a nucleic acid stain (e.g., an oligonucleotide including a label, such as a FAM-labeled oligonucleotide) and measuring the emission of the stain following excitation. In embodiments, the method further includes hybridizing the first extension product to one or more surface-immobilized oligonucleotides immobilized on the surface, prior to or concurrent with the detecting.

In embodiments, the method includes: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; (d) hybridizing the first extension product to one or more surface-immobilized oligonucleotides immobilized on the surface; and (e) detecting the first extension product or a complement thereof by extending a sequencing primer hybridized thereto.

In embodiments, the linear template polynucleotide is generated by joining a first adapter polynucleotide to a 5' end of a sample polynucleotide, and joining a second adapter polynucleotide to a 3' end of the sample polynucleotide. In embodiments, the first adapter polynucleotide includes a portion that hybridizes to the first sequence of the splint primer, and the second adapter polynucleotide includes a portion that hybridizes to the second sequence of the splint primer. Substantially complementary portions of the first adapter polynucleotide and first sequence of the splint primer, and/or second adapter polynucleotide and second sequence of the splint primer, that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In embodiments, the hybridizing sequences are 100% complementary.

In an aspect is a method of amplifying a linear template polynucleotide. In embodiments, the method includes: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide.

In embodiments, the first adapter polynucleotide includes a portion that does not hybridize to the splint primer, wherein after joining to the sample polynucleotide, the portion that hybridizes to the splint primer is distal to the portion that does not hybridize to the splint primer. In embodiments, the second adapter polynucleotide includes a portion that does not hybridize to the splint primer, wherein after joining to the sample polynucleotide, the portion that hybridizes to the splint primer is distal to the portion that does not hybridize to the splint primer. In embodiments, both of the first adapter polynucleotide and the second adapter polynucleotide include a portion that does not hybridize to the splint primer, wherein after joining to the sample polynucleotide, the portion that hybridizes to the splint primer is distal to the portion that does not hybridize to the splint primer.

In embodiments, the portion of the first adapter polynucleotide that does not hybridize to the splint primer includes an index sequence. In embodiments, the portion of the second adapter polynucleotide that does not hybridize to the splint primer includes an index sequence. In embodiments, both the portion of the first adapter polynucleotide that does not hybridize to the splint primer and the portion of the second adapter polynucleotide that does not hybridize to the splint primer includes an index sequence. In embodiments, the index sequence is about or at least about 5, 6, 7, 8, 9, 10, 15, 20, 25, 30, 40, 50, 75 or more nucleotides in length. In embodiments, the index sequence is shorter than 20, 15, 10, 9, 8, 7, 6, or 5 nucleotides in length. In embodiments, the index sequence is 10-50 nucleotides in length, such as 15-40 or 20-30 nucleotides in length. In embodiments, the index sequence is about 5-15 nucleotides in length.

In embodiments, the portion that does not hybridize to the splint primer includes a sequencing primer binding sequence. In embodiments, the sequencing primer binding sequence is between 10 and 40 nucleotides in length. In embodiments, the sequencing primer binding sequence is between 5 and 50 nucleotides in length. In embodiments, the sequencing primer binding sequence is between 10 to 150 nucleotides in length.

In embodiments, the splint primer is about 5 to about 25 nucleotides in length. In embodiments, the splint primer is about 10 to about 40 nucleotides in length. In embodiments, the splint primer is about 5 to about 100 nucleotides in length. In embodiments, the splint primer is about 20 to 200 nucleotides in length. In embodiments, the splint primer is about or at least about 5, 6, 7, 8, 9, 10, 12, 15, 18, 20, 25, 30, 35, 40, 50 or more nucleotides in length.

In embodiments, the first extension product includes a plurality of complements of the circular template polynucleotide. In embodiments, the first extension product includes one complement of the circular template polynucleotide. In embodiments, the first extension product includes two complements of the circular template polynucleotide. In embodiments, the first extension product includes three complements of the circular template polynucleotide. In embodiments, the first extension product includes at least two complements of the circular template polynucleotide.

In embodiments, the surface-immobilized oligonucleotides are a plurality of the surface-immobilized oligonucleotides. In embodiments, the one or more surface-immobilized oligonucleotides hybridize to a complement of: (a) the portion of the first adapter polynucleotide that hybridizes to the first sequence of the splint primer; or (b) the portion of the second adapter polynucleotide that hybridizes to the second sequence of the splint primer. In embodiments, the one or more surface-immobilized oligonucleotides hybridize to a complement of the portion of the first adapter polynucleotide that hybridizes to the first sequence of the splint primer. In embodiments, the one or more surface-immobilized oligonucleotides hybridize to a complement of the portion of the second adapter polynucleotide that hybridizes to the second sequence of the splint primer.

In embodiments, the one or more surface-immobilized oligonucleotides hybridize to a complement of (a) the portion of the first adapter polynucleotide that does not hybridize to the splint primer; or (b) the portion of the second adapter polynucleotide that does not hybridize to the splint primer. In embodiments, the one or more surface-immobilized oligonucleotides hybridize to a complement of the portion of the first adapter polynucleotide that does not hybridize to the splint primer. In embodiments, the one or more surface-immobilized oligonucleotides hybridize to a complement of the portion of the second adapter polynucleotide that does not hybridize to the splint primer.

In embodiments, the one or more surface-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. A blocking moiety can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. Non-limiting examples of 3' blocking groups include a 3'-ONH$_2$ blocking group, a 3'-O-allyl blocking group, or a 3'-O-azidomethyl blocking group. In embodiments, the 3' blocking group is a C3, C9, C12, or C18 spacer phosphoramidite, a 3'phosphate, a C3, C6, C12 amino modifier, or a reversible blocking moiety (e.g., reversible blocking moieties are described in U.S. Pat. Nos. 7,541,444 and 7,057,026). In embodiments, the 3' modification is a 3'-phosphate modification includes a 3' phosphate moiety, which is removed by a PNK enzyme.

In embodiments, circularizing the linear template polynucleotide includes joining the 5' end of the linear template polynucleotide directly to the 3' end of the linear template polynucleotide. In embodiments, circularizing the linear template polynucleotide includes extending the 3' end of the linear template polynucleotide and joining the extended 3' end to the 5' end of the linear template polynucleotide.

In embodiments, circularizing includes a ligation reaction. For example, linear polynucleotides are circularized in a non-template driven reaction with a circularizing ligase, such as Circligase enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., SplintR ligase), and combinations thereof. In embodiments, the two ends of the template polynucleotide are ligated together with the aid of a splint primer that is complementary with the two ends of the template polynucleotide. For example, a T4 ligation reaction may be carried out by combining a linear polynucleotide, ligation buffer, ATP, T4 DNA ligase, water, and incubating the mixture at between about 20° C. to about 45° C., for between about 5 minutes to about 30 minutes. In some embodiments, the T4 ligation reaction is incubated at 37° C. for 30 minutes. In some embodiments, the T4 ligation reaction is incubated at 45° C. for 30 minutes. In embodiments, the ligase reaction is stopped by adding Tris buffer with high EDTA and incubating for 1 minute.

In embodiments, the circular template polynucleotide is about 100 to about 1000 nucleotides in length. In embodiments, the circular template polynucleotide is about 1000 to about 2000 nucleotides in length. In embodiments, the circular template polynucleotide is about 2000 to about 3000 nucleotides in length. In embodiments, the circular template polynucleotide is about 3000 to about 4000 nucleotides in length. In embodiments the circular template polynucleotide is about 4000 to about 5000 nucleotides in length. In embodiments, the circular template polynucleotide is about 100 to about 300 nucleotides in length. In embodiments, the circular template polynucleotide is about 300 to about 500 nucleotides in length. In embodiments, the circular template polynucleotide is about 500 to about 1000 nucleotides in length. In embodiments, the circular template polynucleotide is about 300 to about 600 nucleotides in length. The circular template polynucleotide molecules can vary length, such as about 100-300 nucleotides long, about 300-500 nucleotides long, or about 500-1000 nucleotides long. In embodiments, the circular template polynucleotide molecular is about 100-1000 nucleotides, about 1000-2000 nucleotides, about 2000-3000 nucleotides, about 3000-4000 nucleotides, about 4000-5000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the circular template polynucleotide molecule is about 150 nucleotides. In embodiments, the circular template polynucleotide is about 100-1000 nucleotides long. In embodiments, the circular template polynucleotide is about 1000-2000 nucleotides long. In embodiments, the circular template polynucleotide is about 2000-3000 nucleotides long. In embodiments, the circular template polynucleotide is about 3000-4000 nucleotides long. In embodiments, the circular template polynucleotide is about 4000-5000 nucleotides long. In embodiments, the circular template polynucleotide is about 100-300 nucleotides long. In embodiments, the circular template polynucleotide is about 300-500 nucleotides long. In embodiments, the circular template polynucleotide is about 500-1000 nucleotides long. In embodiments, the circular template polynucleotide molecule is about 100 nucleotides. In embodiments, the circular template polynucleotide molecule is about 300 nucleotides. In embodiments, the circular template polynucleotide molecule is about 500 nucleotides. In embodiments, the circular template polynucleotide molecule is about 1000 nucleotides. In embodiments, the circular template polynucleotide molecule is about 2000 nucleotides. In embodiments, the circular template polynucleotide molecule is about 3000 nucleotides. In embodiments, the circular template polynucleotide molecule is about 4000 nucleotides. In embodiments, the circular template polynucleotide molecule is about 5000 nucleotides.

In embodiments, the linear template polynucleotide includes a genomic sequence of interest. In embodiments, the linear template polynucleotide includes one or more genomic sequences of interest. In embodiments, the linear template polynucleotide includes more than one genomic sequence of interest. In embodiments, the linear template polynucleotide includes cfDNA.

Figure 2A:
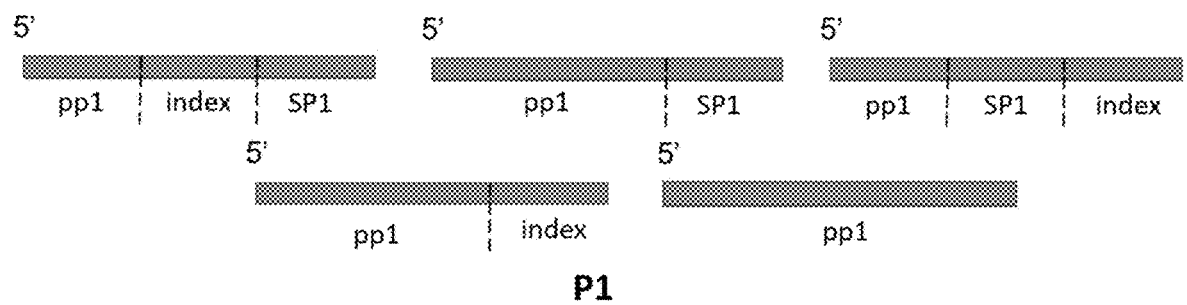
Figure 2B:
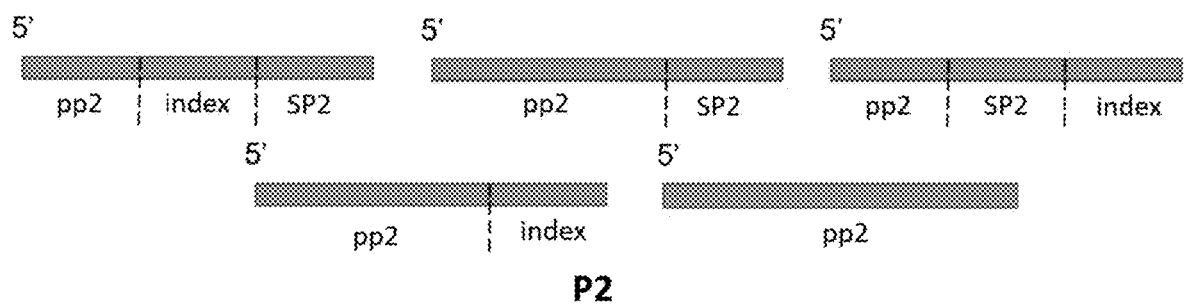

In embodiments, the template polynucleotide includes one or more adapters. An adapter may include a platform primer sequence such as the P5 and P7 sequences, a sequencing primer binding sequence, and optionally one or two barcode/indexes. In embodiments, the template polynucleotide includes two adapters (e.g., an adapter at both the 5' and 3' end of the template polynucleotide. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the adapter includes a hairpin loop structure. In embodiments, the adapter is an adapter described herein, for example in FIGS. 2A-2D. In embodiments, the template polynucleotide has two different adapters ligated at each end, which may be referred to herein as P1 and P2, or the complement thereof, P1' and P2'. In embodiments, the adapters (e.g., P1 and P2) contain a platform priming sequence, referred to as pp1 or pp2, for binding to a flow cell (e.g., commonly used priming sequences P5 and P7 or custom platform priming sequences), and include an optional index sequence (e.g., short oligonucleotide sequences to uniquely tag each molecule in a sample library, and/or to tag every molecule in one library with a sequence that is distinct from sequences used to tag molecules of anther library, alternatively referred to as a sample barcode), and a sequencing primer (SP) site, as illustrated in FIGS. 2A-2B. In embodiments, the adapters further include a platform priming capture (ppC) sequence, as illustrated in FIGS. 2C-2D. The ppC sequences are designed to have a low probability of unintended interactions with other adapters and immobilized oligonucleotides. Additionally, in embodiments, the 5' end of the surface immobilized ppC sequences is phosphorylated for efficient ligation and circularization. In embodiments, the pp1 sequence includes 5'-AATGATACGGCGACCACCG (SEQ ID NO:5) (P5) or the complement thereof. In embodiments the pp2 sequence includes 5'-CAAGCAGAAGACGGCAT-ACGA (SEQ ID NO:6) (P7), or the complement thereof. In embodiments, the sequencing primer is the same. In embodiments, the sequencing primer sequence in P1 is different than the sequencing primer sequence in P2. For example, the sequencing primer sequence in P1 includes a SP1 sequence or the complement thereof and the sequencing primer sequence in P2 includes a SP2 sequence or the complement thereof. Without wishing to be bound by theory, different sequencing primer sequences may have the same or different lengths, the same or different orientations (e.g., the same sequence reversed), and/or different $T_m$.

In embodiments, amplifying the circular template polynucleotide includes incubating the template polynucleotide with the strand-displacing polymerase (a) for about 1 minute to about 2 hours, and/or (b) at a temperature of about 20° C. to about 50° C. In embodiments, the method includes amplifying a template polynucleotide by extending an amplification primer with a strand-displacing polymerase for about 10 seconds to about 30 minutes. In embodiments, the method includes amplifying a template polynucleotide by extending an amplification primer with a strand-displacing polymerase for about 30 seconds to about 16 minutes. In embodiments, the method includes amplifying a template polynucleotide by extending an amplification primer with a strand-displacing polymerase for about 30 seconds to about 10 minutes. In embodiments, the method includes amplifying a template polynucleotide by extending an amplification primer with a strand-displacing polymerase for about 30 seconds to about 5 minutes. In embodiments, the method includes amplifying a template polynucleotide by extending an amplification primer with a strand-displacing polymerase for about 1 second to about 5 minutes. In embodiments, the method includes amplifying a template polynucleotide by extending an amplification primer with a strand-displacing polymerase for about 1 second to about 2 minutes.

In embodiments, the method includes amplifying a template polynucleotide by extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C.

In embodiments, the strand-displacing polymerase is a phi29 polymerase, a phi29 mutant polymerase, or a thermostable phi29 mutant polymerase. In embodiments, the strand-displacing enzyme is a SD polymerase (or mutant thereof), Bst large fragment polymerase (or mutant thereof), or a phi29 polymerase (or mutant thereof). A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase phototolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase comprising at least one mutation selected from the group consisting of M8R, V51A, M97T, L123S, G197D, K209E, E221K, E239G, Q497P, K512E, E515A, and F526 (relative to wild type phi29 polymerase).

In embodiments, amplifying includes rolling circle amplification (RCA) (see, e.g., Lizardi et al., Nat. Genet. 19:225-232 (1998), which is incorporated herein by reference in its entirety). Several suitable RCA methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer). In embodiments, amplifying includes exponential rolling circle amplification (eRCA). Exponential RCA is similar to the linear process except that it uses a second primer (e.g., one or more surface-immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)). In embodiments, amplifying includes hyperbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

In embodiments, amplifying includes at least two distinct amplification phases (i.e., two distinct types of amplification methods). For example, amplifying includes i) a rolling circle amplification method and ii) a PCR amplification method. In a first amplification phase, a first extension product containing one or more copies of the initial nucleic acid template molecule (also referred to herein as an amplicon or concatemer) is made with the use of a splint primer, nucleotides, and a DNA polymerase (e.g., strand-displacing DNA polymerase). Subsequently, the first extension product participates in a second amplification phase in which multiple copies of the initial amplicon or amplicons are made (i.e., a second amplification product) via the hybridization of their respective free 3' end(s) to other surface-immobilized oligonucleotides or to a complementary fraction of another amplicon, followed by extension by a DNA polymerase. During this second amplification phase, amplicons can be copied and result in nucleic acid molecules of the same length, or amplicons can hybridize to a complementary region of other DNA amplicons, thereby making the participating amplicons longer during the process. On a surface with multiple concatemers, both types of extension events may occur for different individual molecules during a given cycle, and over the course of many cycles, a given concatemer may participate in both types of extension events. In embodiments, the amplification method includes (a) amplifying a circular template polynucleotide by extending the splint primer with a strand-displacing polymerase, wherein the splint primer extension generates a first extension product including one or more complement(s) of the circular template polynucleotide; and (b) amplifying the first extension product or a complement thereof on a solid support including a plurality of surface-immobilized oligonucleotides attached to the solid support, wherein the surface-immobilized oligonucleotides include a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, the strand-displacing polymerase is removed or inactivated prior to step (b). In embodiments, the method includes cleaving the first extension product prior to step (b).

In embodiments, step (b) includes bridge amplification; for example as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers (i.e., surface-immobilized oligonucleotides) are attached to the solid support, the extension products released upon separation from an initial template are also attached to the solid support. Both strands are immobilized on the solid support at the 5' end, preferably via a covalent attachment. The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing a polymerase in buffer conditions that allow primer annealing and extension. In embodiments, forward and/or reverse primers hybridize to primer binding sites that are specific to a particular target nucleic acid sequence present in the first extension product of step (a). In embodiments, forward and/or reverse primers hybridize to primer binding sites that are common among different first extension products of step (a).

In embodiments, the first extension product includes at least one cleavable site (e.g., a cleavable site as described herein). In embodiments, the at least one cleavable site includes deoxyuracil triphosphate (dUTP). The enzyme uracil DNA glycosylase (UDG) may then be used to remove dUTP, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In embodiments, the USER™ reagent available from New England Biolabs (NEB catalog #M5508) is used for the creation of a single nucleotide gap at a uracil base in a duplex strand. In embodiments, the first extension product is cleaved at the at least one cleavable site prior to sequencing.

In embodiments, cleavage of the first extension product including a cleavable site, for example, including one or more uracils, may be accomplished using a cleavage mixture including about 150 mM to about 300 mM glycine-KOH, about 5 mM to about 15 mM MgCl2, about 0.05% to about 0.15% Triton X-100, and about 0.05 U/uL to about 0.2 U/uL uracil DNA glycosylase (UDG). In embodiments, the cleavage mixture can have a pH greater than pH 8.0, greater than pH 8.5, greater than pH 9.0, greater than pH 9.5, or greater than pH 10.0. In other embodiments, the cleavage mixture can have a pH ranging, for example, from about pH 8.0 to about pH 10.0, from about pH 8.5 to about pH 10.0, or from about pH 9.0 to about pH 10.0. For example, the cleavage mixture is applied to an immobilized oligonucleotide including one or more uracils, incubated at about 37° C. to about 42° C. for 10 min, and then incubated at about 65° C. to about 72° C. for 30 min. Following cleavage, the surface is washed with wash buffer, followed by subsequent washes with about 0.05M NaOH to about 0.15M NaOH, and another wash with wash buffer.

In embodiments, the splint primer is attached to the solid support (i.e., immobilized on the surface of a solid support). Splint primer molecules can be fixed to surface by a variety of techniques, including covalent attachment and non-covalent attachment. In embodiments, the splint primers are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have primers that exceeds the amount or concentration present at the interstitial regions. In some embodiments the primers may not be present at the interstitial regions. In embodiments, the splint primer is attached to a solid support and a circular template polynucleotide is hybridized to the splint primer. In embodiments, at least two different primers are attached to the solid support (e.g., a forward and a reverse primer), which facilitates generating multiple amplification products from the first extension product or a complement thereof. In embodiments, the splint primer includes a cleavable site and may be cleaved, thereby removing the amplification product from the substrate.

In embodiments of the methods provided herein, the clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values. In embodiments, the mean or median diameter is about 100-3000 nanometers. In embodiments, the mean or median diameter is about 100-2000 nanometers. In embodiments, the mean or median diameter is about 500-2500 nanometers. In embodiments, the mean or median diameter is about 200-1000 nanometers. In embodiments, the mean or median diameter is about 1000-2000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 1000 nanometers. In embodiments, the mean or median diameter is about or at most about 2000 nanometers. In embodiments, the mean or median diameter is about or at most about 2500 nanometers. In embodiments, the mean or median diameter is about or at most about 3000 nanometers.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about 100, 200, 300, 400, 500, 600, 700, 800, 900, 1000, 1100, 1200, 1300, 1400, 1500, 1600, 1700, 1800, 1900, 2000 nanometers or a number or a range between any two of these values. In embodiments, the mean or median diameter is about 100-3000 nanometers. In embodiments, the mean or median diameter is about 100-2000 nanometers. In embodiments, the mean or median diameter is about 500-2500 nanometers. In embodiments, the mean or median diameter is about 200-1000 nanometers. In embodiments, the mean or median diameter is about 1000-2000 nanometers. In embodiments, the mean or median diameter is about 100 nanometers. In embodiments, the mean or median diameter is about 200 nanometers. In embodiments, the mean or median diameter is about 500 nanometers. In embodiments, the mean or median diameter is about 1000 nanometers. In embodiments, the mean or median diameter is about 2000 nanometers. In embodiments, the mean or median diameter is about 2500 nanometers. In embodiments, the mean or median diameter is about 3000 nanometers.

In embodiments, the method does not include extending the one or more surface-immobilized oligonucleotides. For example, the one or more surface-immobilized oligonucleotides may be used to aid in tethering the extension product to the substrate and may not be extended. For example, the 3' ends of the surface-immobilized oligonucleotides may be rendered unextendible by including a blocking group at their 3' ends that prevent polymerase extension. A blocking moiety prevents formation of a covalent bond between the 3' hydroxyl moiety of the nucleotide and the 5' phosphate of another nucleotide. A blocking moiety can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. Non-limiting examples of 3' blocking groups include a 3'-$ONH_2$ blocking group, a 3'-O-allyl blocking group, or a 3'-O-azidomethyl blocking group. In embodiments, the 3' blocking group is a C3, C9, C12, or C18 spacer phosphoramidite, a 3'phosphate, a C3, C6, C12 amino modifier, or a reversible blocking moiety (e.g., reversible blocking moieties are described in U.S. Pat. Nos. 7,541,444 and 7,057,026). In embodiments, the 3' modification is a 3'-phosphate modification includes a 3' phosphate moiety, which is removed by a PNK enzyme.

In embodiments, the method further includes extending the one or more surface-immobilized oligonucleotides hybridized to the first extension product with a polymerase. For example, the one or more surface-immobilized oligonucleotides may be used to aid in tethering the extension product to the substrate and may be extended in an exponential RCA amplification reaction. In embodiments, the method further includes removing the blocking groups and extending the surface-immobilized oligonucleotides hybridized to the first extension product with a polymerase.

In embodiments, the sequencing primer hybridizes to a complement of: (a) the portion of the first adapter polynucleotide that hybridizes to the first sequence of the splint primer; or (b) the portion of the second adapter polynucleotide that hybridizes to the second sequence of the splint primer. In embodiments, the sequencing primer hybridizes to a complement of the portion of the first adapter polynucleotide that hybridizes to the first sequence of the splint primer. In embodiments, the sequencing primer hybridizes to a complement of the portion of the second adapter polynucleotide that hybridizes to the second sequence of the splint primer.

In embodiments, the sequencing primer hybridizes to a complement of: (a) the portion of the first adapter polynucleotide that does not hybridize to the splint primer; or (b) the portion of the second adapter polynucleotide that does not hybridize to the splint primer. In embodiments, the sequencing primer hybridizes to a complement of the portion of the first adapter polynucleotide that does not hybridize to the splint primer. In embodiments, the sequencing primer hybridizes to a complement of the portion of the second adapter polynucleotide that does not hybridize to the splint primer.

In embodiments, sequencing includes extending the sequencing primer(s) by incorporating with a polymerase one or more nucleotides or nucleotide analogues into the sequencing primer and detecting the incorporated nucleotides or nucleotide analogues. The identity of the incorporated nucleotide provides information sequence information of the polynucleotide being sequenced. In embodiments, the method includes detecting the first extension product or a complement thereof by extending a sequencing primer hybridized thereto.

In embodiments, the method includes sequencing the extension product(s) or a complement thereof by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and optionally repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. In embodiments, each nucleotide (i.e., dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); is labeled with a unique fluorescent dye relative to each other. A variety of sequencing chemistries are available, non-limiting examples of which are described herein.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US 2018/0274024, WO 2017/205336, US 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

The methods and kits of the present disclosure may be applied, mutatis mutandis, to the sequencing of RNA, or to determining the identity of a ribonucleotide.

IV. Methods of Selectively Capturing and Methods of Selectively Sequencing

In an aspect is provided herein a method of selectively sequencing a linear template polynucleotide, the method including (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) hybridizing a probe oligonucleotide to the circular template polynucleotide from step (b); (d) separating the probe-hybridized circular template polynucleotide from template polynucleotides not hybridized to a probe; and (e) sequencing the probe-hybridized circular template polynucleotide of step (d).

In embodiments, the method further comprises, prior to sequencing, amplifying the probe-hybridized circular template polynucleotide. In embodiments, the method includes immobilizing the amplification products on a solid support. In embodiments, the method includes providing a solid support including a plurality of immobilized oligonucleotide primers attached to the solid support via a linker, wherein the plurality of oligonucleotide primers include a plurality of forward primers and a plurality of reverse primers, amplifying the amplification products by using the oligonucleotide primers attached to the solid support to generate a plurality of double-stranded amplification products.

In an aspect is a method of amplifying a linear template polynucleotide. In embodiments, the method includes: (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide.

In an aspect is provided herein a method of selectively sequencing a linear template polynucleotide, the method including (a) hybridizing the linear template polynucleotide to a splint primer immobilized on a surface, wherein (i) the splint primer includes, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide including a continuous strand lacking free 5' and 3' ends; (c) amplifying the circular template polynucleotide by extending the splint primer with a strand-displacing polymerase, wherein the extension generates a first extension product including one or more complements of the circular template polynucleotide; (d) hybridizing a probe oligonucleotide to the first extension product from step (c); (e) separating the probe-hybridized extension product from extension products not hybridized to a probe; and (f) sequencing the probe-hybridized extension product of step (e).

In embodiments, the linear template polynucleotide is generated by joining a first adapter polynucleotide to a 5' end of a sample polynucleotide, and joining a second adapter polynucleotide to a 3' end of the sample polynucleotide. In embodiments, the first adapter polynucleotide includes a portion that hybridizes to the first sequence of the splint primer, and the second adapter polynucleotide includes a portion that hybridizes to the second sequence of the splint primer. Substantially complementary portions of the first adapter polynucleotide and first sequence of the splint primer, and/or second adapter polynucleotide and second sequence of the splint primer, that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In embodiments, the hybridizing sequences are 100% complementary.

In embodiments, the method further comprises, prior to sequencing, amplifying the probe-hybridized extension products. In embodiments, the method includes immobilizing the amplification products on a solid support. In embodiments, the method includes providing a solid support including a plurality of immobilized oligonucleotide primers attached to the solid support via a linker, wherein the plurality of oligonucleotide primers include a plurality of forward primers and a plurality of reverse primers, amplifying the amplification products by using the oligonucleotide primers attached to the solid support to generate a plurality of double-stranded amplification products.

In embodiments, generating an amplification product includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, generating a double-stranded amplification product includes a bridge polymerase chain reaction amplification. In embodiments, generating an amplification product includes a thermal bridge polymerase chain reaction (t-bPCR) amplification. In embodiments, generating an amplification product includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions.

In embodiments, the probe oligonucleotide acts as a primer. In embodiments, the probe oligonucleotide contains a sequence capable of hybridizing to a mutated sequence (i.e., a hotspot sequence) as identified in Catalogue of Somatic Mutations In Cancer (COSMIC), full-length genes, copy number genes, single nucleotide polymorphisms (SNPs), or inter- and intragenic gene fusions. In embodiments, the probe oligonucleotide contains a sequence capable of hybridizing to a region of interest, such as a gene associated with cancer (e.g., lung, colon, breast, ovarian, melanoma, or prostate cancer) see for example Simen B B, Arch Pathol Lab Med; 139(4):508-517 (2015) or Singh R R, J Mol Diagn. September; 15(5):607-22 (2013); a gene associated with a disease (e.g., retinopathy, epilepsy, immunodeficiency, cardiomyopathy, hearing loss, muscular dystrophy, aneuploidy), see for example S. Yohe et al. Vol. 139, No. 2, pp. 204-210 (2015) or Rehm H L. Nat Rev Genet. 14(4):295-300 (2013); or a gene associated with persisting pain (see for example Kringel et al. Front. Pharmacol. V9 Art. 1008 2018).

In embodiments, the probe oligonucleotide includes a sequence capable of hybridizing to an oncogene and/or tumor suppressor gene sequence, or a portion thereof. Non-limiting examples of oncogenes and tumor suppressor genes include the ABL1 gene, AKT1 gene, ALK gene, APC gene, ATM gene, BRAF gene, BRCA gene, CDH1 gene, CDKN2A gene, CSF1R gene, CTNNB1 gene, EGFR gene, ERBB2 gene, ERBB4 gene, EZH2 gene, FBXW7 gene, FGFR1 gene, FGFR2 gene, FGFR3 gene, FLT3 gene, GNA11 gene, GNAQ gene, GNAS gene, HNF1A gene, HRAS gene, IDH1 gene, IDH2 gene, JAK2 gene, JAK3 gene, KDR gene, KIT gene, KRAS gene, MET gene, MLH1 gene, MPL gene, NOTCH1 gene, NPM1 gene, NRAS gene, PDGFRA gene, PIK3CA gene, PTEN gene, PTPN11 gene, RB1 gene, RET gene, SMAD4 gene, SMARCB1 gene, SMO gene, SRC gene, STK11 gene, TP53 gene, VHL gene, or a portion thereof.

In embodiments, the first adapter polynucleotide includes a portion that does not hybridize to the splint primer, wherein after joining to the sample polynucleotide, the portion that hybridizes to the splint primer is distal to the portion that does not hybridize to the splint primer. In embodiments, the second adapter polynucleotide includes a portion that does not hybridize to the splint primer, wherein after joining to the sample polynucleotide, the portion that hybridizes to the splint primer is distal to the portion that does not hybridize to the splint primer. In embodiments, both of the first adapter polynucleotide and the second adapter polynucleotide include a portion that does not hybridize to the splint primer, wherein after joining to the sample polynucleotide, the portion that hybridizes to the splint primer is distal to the portion that does not hybridize to the splint primer.

In embodiments, the portion of the first adapter polynucleotide that does not hybridize to the splint primer includes an index sequence. In embodiments, the portion of the second adapter polynucleotide that does not hybridize to the splint primer includes an index sequence. In embodiments, both the portion of the first adapter polynucleotide that does not hybridize to the splint primer and the portion of the second adapter polynucleotide that does not hybridize to the splint primer includes an index sequence. In embodiments, the index sequence is about or at least about 5, 6, 7, 8, 9, 10, 15, 20, 25, 30, 40, 50, 75 or more nucleotides in length. In embodiments, the index sequence is shorter than 20, 15, 10, 9, 8, 7, 6, or 5 nucleotides in length. In embodiments, the index sequence is 10-50 nucleotides in length, such as 15-40 or 20-30 nucleotides in length. In embodiments, the index sequence is about 5-15 nucleotides in length.

In embodiments, the portion that does not hybridize to the splint primer includes a sequencing primer binding sequence. In embodiments, the sequencing primer binding sequence is between 10 and 40 nucleotides in length. In embodiments, the sequencing primer binding sequence is between 5 and 50 nucleotides in length. In embodiments, the sequencing primer binding sequence is between 10 to 150 nucleotides in length.

In embodiments, the splint primer is about 5 to about 25 nucleotides in length. In embodiments, the splint primer is about 10 to about 40 nucleotides in length. In embodiments, the splint primer is about 5 to about 100 nucleotides in length. In embodiments, the splint primer is about 20 to 200 nucleotides in length. In embodiments, the splint primer is about or at least about 5, 6, 7, 8, 9, 10, 12, 15, 18, 20, 25, 30, 35, 40, 50 or more nucleotides in length.

In embodiments, the first extension product includes a plurality of complements of the circular template polynucleotide. In embodiments, the first extension product includes one complement of the circular template polynucleotide. In embodiments, the first extension product includes two complements of the circular template polynucleotide. In embodiments, the first extension product includes three complements of the circular template polynucleotide. In embodiments, the first extension product includes at least two complements of the circular template polynucleotide.

In embodiments, the surface-immobilized oligonucleotides are a plurality of the surface-immobilized oligonucleotides. In embodiments, the one or more surface-immobilized oligonucleotides hybridize to a complement of: (a) the portion of the first adapter polynucleotide that hybridizes to the first sequence of the splint primer; or (b) the portion of the second adapter polynucleotide that hybridizes to the second sequence of the splint primer. In embodiments, the one or more surface-immobilized oligonucleotides hybridize to a complement of the portion of the first adapter polynucleotide that hybridizes to the first sequence of the splint primer. In embodiments, the one or more surface-immobilized oligonucleotides hybridize to a complement of the portion of the second adapter polynucleotide that hybridizes to the second sequence of the splint primer.

In embodiments, the one or more surface-immobilized oligonucleotides hybridize to a complement of (a) the portion of the first adapter polynucleotide that does not hybridize to the splint primer; or (b) the portion of the second adapter polynucleotide that does not hybridize to the splint primer. In embodiments, the one or more surface-immobilized oligonucleotides hybridize to a complement of the portion of the first adapter polynucleotide that does not hybridize to the splint primer. In embodiments, the one or more surface-immobilized oligonucleotides hybridize to a complement of the portion of the second adapter polynucleotide that does not hybridize to the splint primer.

In embodiments, the one or more surface-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. A blocking moiety can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. Non-limiting examples of 3' blocking groups include a 3'-ONH$_2$ blocking group, a 3'-O-allyl blocking group, or a 3'-O-azidomethyl blocking group. In embodiments, the 3' blocking group is a C3, C9, C12, or C18 spacer phosphoramidite, a 3'phosphate, a C3, C6, C12 amino modifier, or a reversible blocking moiety (e.g., reversible blocking moieties are described in U.S. Pat. Nos. 7,541,444 and 7,057,026). In embodiments, the 3' modification is a 3'-phosphate modification includes a 3' phosphate moiety, which is removed by a PNK enzyme.

In embodiments, circularizing the linear template polynucleotide includes joining the 5' end of the linear template polynucleotide directly to the 3' end of the linear template polynucleotide. In embodiments, circularizing the linear template polynucleotide includes extending the 3' end of the linear template polynucleotide and joining the extended 3' end to the 5' end of the linear template polynucleotide.

In embodiments, circularizing includes a ligation reaction. For example, linear polynucleotides are circularized in a non-template driven reaction with a circularizing ligase, such as CircLigase, Taq DNA Ligase, HiFi Taq DNA Ligase, T4 DNA ligase, or Ampligase® DNA Ligase. In embodiments, the two ends of the template polynucleotide are ligated together with the aid of a splint primer that is complementary with the two ends of the template polynucleotide. For example, a T4 ligation reaction may be carried out by combining a linear polynucleotide, ligation buffer, ATP, T4 DNA ligase, water, and incubating the mixture at between about 20° C. to about 45° C., for between about 5 minutes to about 30 minutes. In some embodiments, the T4 ligation reaction is incubated at 37° C. for 30 minutes. In some embodiments, the T4 ligation reaction is incubated at 45° C. for 30 minutes. In embodiments, the ligase reaction is stopped by adding Tris buffer with high EDTA and incubating for 1 minute.

In embodiments, the circular template polynucleotide is about 100 to about 1000 nucleotides in length. In embodiments, the circular template polynucleotide is about 1000 to about 2000 nucleotides in length. In embodiments, the circular template polynucleotide is about 2000 to about 3000 nucleotides in length. In embodiments, the circular template polynucleotide is about 3000 to about 4000 nucleotides in length. In embodiments the circular template polynucleotide is about 4000 to about 5000 nucleotides in length. In embodiments, the circular template polynucleotide is about 100 to about 300 nucleotides in length. In embodiments, the circular template polynucleotide is about 300 to about 500 nucleotides in length. In embodiments, the circular template polynucleotide is about 500 to about 1000 nucleotides in length. In embodiments, the circular template polynucleotide is about 300 to about 600 nucleotides in length. The circular template polynucleotide molecules can vary length, such as about 100-300 nucleotides long, about 300-500 nucleotides long, or about 500-1000 nucleotides long. In embodiments, the circular template polynucleotide molecular is about 100-1000 nucleotides, about 1000-2000 nucleotides, about 2000-3000 nucleotides, about 3000-4000 nucleotides, about 4000-5000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the circular template polynucleotide molecule is about 150 nucleotides. In embodiments, the circular template polynucleotide is about 100-1000 nucleotides long. In embodiments, the circular template polynucleotide is about 1000-2000 nucleotides long. In embodiments, the circular template polynucleotide is about 2000-3000 nucleotides long. In embodiments, the circular template polynucleotide is about 3000-4000 nucleotides long. In embodiments, the circular template polynucleotide is about 4000-5000 nucleotides long. In embodiments, the circular template polynucleotide is about 100-300 nucleotides long. In embodiments, the circular template polynucleotide is about 300-500 nucleotides long. In embodiments, the circular template polynucleotide is about 500-1000 nucleotides long. In embodiments, the circular template polynucleotide molecule is about 100 nucleotides. In embodiments, the circular template polynucleotide molecule is about 300 nucleotides. In embodiments, the circular template polynucleotide molecule is about 500 nucleotides. In embodiments, the circular template polynucleotide molecule is about 1000 nucleotides. In embodiments, the circular template polynucleotide molecule is about 2000 nucleotides. In embodiments, the circular template polynucleotide molecule is about 3000 nucleotides. In embodiments, the circular template polynucleotide molecule is about 4000 nucleotides. In embodiments, the circular template polynucleotide molecule is about 5000 nucleotides.

In embodiments, the template polynucleotide includes one or more adapters. In embodiments, the template polynucleotide includes two adapters. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the adapter includes a hairpin loop structure. In embodiments, the adapter is an adapter described herein, for example in FIGS. 2A-2D. In embodiments, the template polynucleotide has two different adapters ligated at each end, which may be referred to herein as P1 and P2, or the complement thereof, P1' and P2'. In embodiments, the adapters (e.g., P1 and P2) contain a platform priming sequence, referred to as pp1 or pp2, for binding to a flow cell (e.g., commonly used priming sequences P5 and P7 or custom platform priming sequences), and include an optional index sequence (e.g., short oligonucleotide sequences to uniquely tag each molecule in a sample library, and/or to tag every molecule in one library with a sequence that is distinct from sequences used to tag molecules of anther library, alternatively referred to as a sample barcode), and a sequencing primer (SP) site, as illustrated in FIGS. 2A-2B. In embodiments, the adapters further include a platform priming capture (ppC) sequence, as illustrated in FIGS. 2C-2D. The ppC sequences are designed to have a low probability of unintended interactions with other adapters and immobilized oligonucleotides. Additionally, in embodiments, the 5' end of the surface immobilized ppC sequences is phosphorylated for efficient ligation and circularization. In embodiments, the pp1 sequence includes 5'-AATGATACGGCGACCACCG (SEQ ID NO:5) (P5) or the complement thereof. In embodiments the pp2 sequence includes 5'-CAAGCAGAAGACGGCATACGA (SEQ ID NO:6) (P7), or the complement thereof. In embodiments, the sequencing primer is the same. In embodiments, the sequencing primer in P1 is different than the sequencing primer in P2.

In embodiments, amplifying the circular template polynucleotide includes incubating the template polynucleotide with the strand-displacing polymerase (a) for about 1 minute to about 2 hours, and/or (b) at a temperature of about 20° C. to about 50° C. In embodiments, the method includes amplifying a template polynucleotide by extending an amplification primer with a strand-displacing polymerase for about 10 seconds to about 30 minutes. In embodiments, the method includes amplifying a template polynucleotide by extending an amplification primer with a strand-displacing polymerase for about 30 seconds to about 16 minutes. In embodiments, the method includes amplifying a template polynucleotide by extending an amplification primer with a strand-displacing polymerase for about 30 seconds to about 10 minutes. In embodiments, the method includes amplifying a template polynucleotide by extending an amplification primer with a strand-displacing polymerase for about 30 seconds to about 5 minutes. In embodiments, the method includes amplifying a template polynucleotide by extending an amplification primer with a strand-displacing polymerase for about 1 second to about 5 minutes. In embodiments, the method includes amplifying a template polynucleotide by extending an amplification primer with a strand-displacing polymerase for about 1 second to about 2 minutes. In embodiments, the method includes amplifying a template polynucleotide by extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C.

In embodiments, the strand-displacing polymerase is a phi29 polymerase, a phi29 mutant polymerase, or a thermostable phi29 mutant polymerase. In embodiments, the strand-displacing enzyme is an SD polymerase, Bst large fragment polymerase, or a phi29 polymerase or mutant thereof. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, D15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase photo-tolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase comprising at least one mutation selected from the group consisting of M8R, V51A, M97T, L123S, G197D, K209E, E221K, E239G, Q497P, K512E, E515A, and F526 (relative to wild type phi29 polymerase).

In embodiments, amplifying includes rolling circle amplification (RCA) (see, e.g., Lizardi et al., Nat. Genet. 19:225-232 (1998), which is incorporated herein by reference in its entirety). Several suitable RCA methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer). In embodiments, amplifying includes exponential rolling circle amplification (eRCA). Exponential RCA is similar to the linear process except that it uses a second primer (e.g., one or more surface-immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)). In embodiments, amplifying includes hyperbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

In embodiments, amplifying includes at least two distinct amplification phases. In a first amplification phase, a first extension product containing one or more copies of the initial nucleic acid template molecule (also referred to herein as an amplicon or concatemer) is made with the use of a splint primer, nucleotides, and a DNA polymerase (e.g., strand-displacing DNA polymerase). Subsequently, the first extension product participates in a second amplification phase in which multiple copies of the initial amplicon or amplicons are made (i.e., a second amplification product) via the hybridization of their respective free 3' end(s) to other surface-immobilized oligonucleotides or to a complementary fraction of another amplicon, followed by extension by a DNA polymerase. During this second amplification phase, amplicons can be copied and result in nucleic acid molecules of the same length, or amplicons can hybridize to a complementary region of other DNA amplicons, thereby making the participating amplicons longer during the process. On a surface with multiple concatemers, both types of extension events may occur for different individual molecules during a given cycle, and over the course of many cycles, a given concatemer may participate in both types of extension events. In embodiments, the amplification method includes (a) amplifying a circular template polynucleotide by extending the splint primer with a strand-displacing polymerase, wherein the splint primer extension generates a first extension product including one or more complement(s) of the circular template polynucleotide; and (b) amplifying the first extension product or a complement thereof on a solid support including a plurality of surface-immobilized oligonucleotides attached to the solid support, wherein the surface-immobilized oligonucleotides include a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, the strand-displacing polymerase is removed or inactivated prior to step (b). In embodiments, the method includes cleaving the first extension product prior to step (b).

In embodiments, step (b) includes bridge amplification; for example, as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers (i.e., surface-immobilized oligonucleotides) are attached to the solid support, the extension products released upon separation from an initial template are also attached to the solid support. Both strands are immobilized on the solid support at the 5' end, preferably via a covalent attachment. The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing a polymerase in buffer conditions that allow primer annealing and extension. In embodiments, forward and/or reverse primers hybridize to primer binding sites that are specific to a particular target nucleic acid sequence present in the first extension product of step (a). In embodiments, forward and/or reverse primers hybridize to primer binding sites that are common among different first extension products of step (a).

In embodiments, the first extension product includes at least one cleavable site (e.g., a cleavable site as described herein). In embodiments, the at least one cleavable site includes deoxyuracil triphosphate (dUTP). The enzyme uracil DNA glycosylase (UDG) may then be used to remove dUTP, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In embodiments, the USER™ reagent available from New England Biolabs (NEB catalog #M5508) is used for the creation of a single nucleotide gap at a uracil base in a duplex strand. In embodiments, the first extension product is cleaved at the at least one cleavable site prior to sequencing.

In embodiments, the splint primer is attached to the solid support (i.e., immobilized on the surface of a solid support). Splint primer molecules can be fixed to surface by a variety of techniques, including covalent attachment and non-covalent attachment. In embodiments, the splint primers are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have primers that exceeds the amount or concentration present at the interstitial regions. In some embodiments the primers may not be present at the interstitial regions. In embodiments, the splint primer is attached to a solid support and a circular template polynucleotide is hybridized to the splint primer. In embodiments, at least two different primers are attached to the solid support (e.g., a forward and a reverse primer), which facilitates generating multiple amplification products from the first extension product or a complement thereof.

In embodiments, the probe oligonucleotide is covalently attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous. In embodiments, the probe oligonucleotide is covalently attached to a bead.

In embodiments, the probe is complementary to 10, 15, 20, 25, 50, 75, 120, or more consecutive nucleotides of the circular template polynucleotide. In embodiments, the probe is complementary to 10 consecutive nucleotides of the circular template polynucleotide. In embodiments, the probe is complementary to 10, or more consecutive nucleotides of the circular template polynucleotide. In embodiments, the probe is complementary to 15 consecutive nucleotides of the circular template polynucleotide. In embodiments, the probe is complementary to 15, or more consecutive nucleotides of the circular template polynucleotide. In embodiments, the probe is complementary to 20 consecutive nucleotides of the circular template polynucleotide. In embodiments, the probe is complementary to 20, or more consecutive nucleotides of the circular template polynucleotide. In embodiments, the probe is complementary to 25 consecutive nucleotides of the circular template polynucleotide. In embodiments, the probe is complementary to 25, or more consecutive nucleotides of the circular template polynucleotide. In embodiments, the probe is complementary to 50 consecutive nucleotides of the circular template polynucleotide. In embodiments, the probe is complementary to 50, or more consecutive nucleotides of the circular template polynucleotide. In embodiments, the probe is complementary to 75 consecutive nucleotides of the circular template polynucleotide. In embodiments, the probe is complementary to 75, or more consecutive nucleotides of the circular template polynucleotide. In embodiments, the probe is complementary to 120 consecutive nucleotides of the circular template polynucleotide. In embodiments, the probe is complementary to 120, or more consecutive nucleotides of the circular template polynucleotide. In embodiments, the probe is complementary to about 15 to about 60 consecutive nucleotides of the circular template polynucleotide. In embodiments, the probe is complementary to about 20 to about 50 consecutive nucleotides of the circular template polynucleotide. In embodiments, the probe is complementary to about 30 to about 40 consecutive nucleotides of the circular template polynucleotide.

In embodiments, a plurality of different probe oligonucleotides are utilized during the hybridizing step, such that multiple target polynucleotides having different sequences are processed simultaneously.

In embodiments, the sequencing comprises sequencing according to any of the aspects described herein, including with respect to methods of sequencing described above.

EXAMPLES

Example 1. Circularizing ssDNA on a Solid Support

Rolling circle amplification (RCA) can use a single-stranded circular (ssc) DNA template to produce a single-stranded linear concatemer consisting of tandem repeats of the same sequence. RCA has a wide variety of applications in biotechnology, such as clonal amplification of DNA libraries in preparation for DNA sequencing. Example methods of library preparation for sequencing include the conversion of linear sequencing libraries into ssc templates, and involve a ligation, purification, and exonuclease treatment that increase library preparation time and overall user burden. Circularization of linear templates on a surface followed by amplification to generate monoclonal clusters for NGS-applications results in greater amplification workflow efficiency without a need for the purification step or exonuclease treatment. This simplifies library preparation without sacrificing sequencing quality.

Figure 1B:
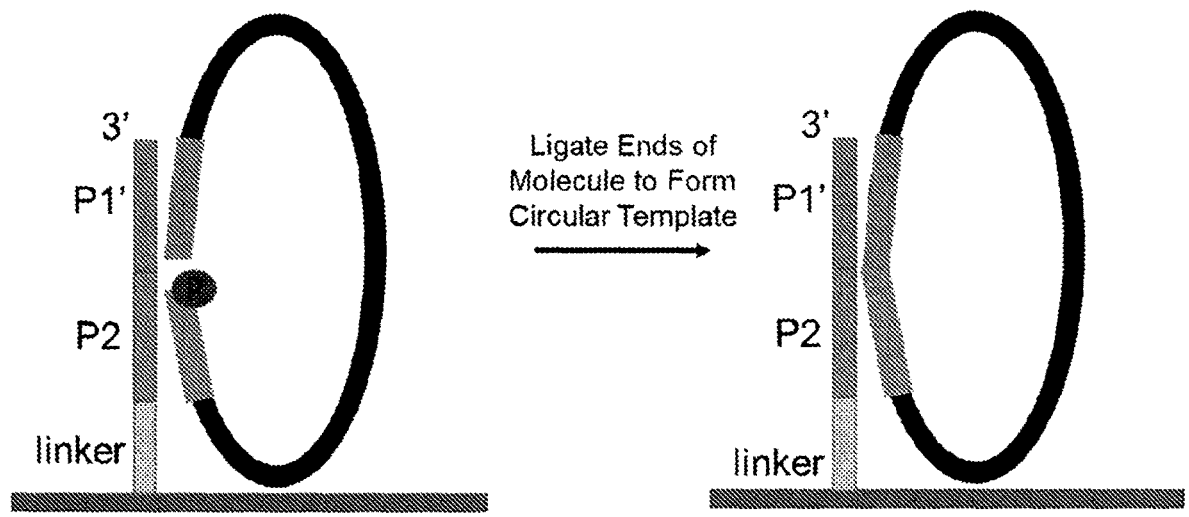
Figure 1C:
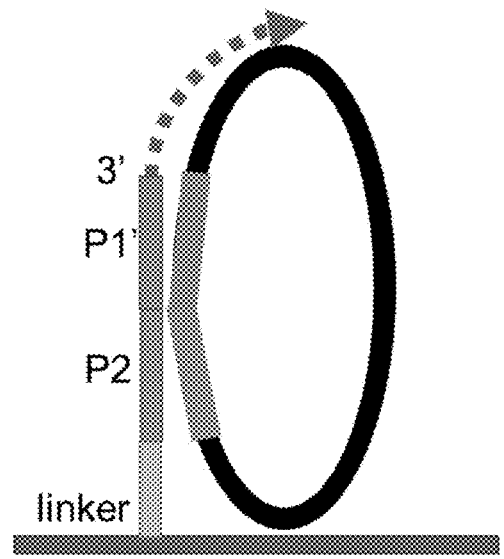
Figure 1D:

A schematic showing the overall process for circularizing and amplifying linear single-stranded (ss) templates by circular amplification techniques on-surface is shown in FIGS. 1A-1C. Depicted in FIG. 1A, the target ssDNA is (1) single-stranded, (2) has adapters which contain sequences complementary to surface-immobilized oligo sequences, and (3) optionally contains a 5' phosphate required for ligation. Standard NGS-library preparation methods (e.g., AmpliSeq Library Prep kits) typically result in double-stranded DNA molecules that do not contain a 5' phosphate. These molecules may be converted to single strands (e.g., via addition of chemical denaturants or increasing the temperature to denature the double strands) and phosphorylated (e.g., T4 PNK phosphorylation) according to known techniques in the art. Alternatively, the ssDNA may be phosphorylated following hybridization to the splint primer.

As described above, the target ssDNA has two different adapters ligated at each end, which may be referred to herein as P1 and P2, or the complement thereof, P1' and P2'. The adapters are ligated onto the 5' end and the 3' end of the ssDNA template, referred to herein as the 5'-adapter and the 3'-adapter, respectively. In FIG. 1A, the 5'-adapter is represented as P2' and the 3'-adapter is represented as P1. The adapters P1 and P2 contain a platform priming sequence, referred to as pp1 or pp2, for binding to a flow cell (e.g., commonly used priming sequences P5 and P7 or custom priming sequences), and include an optional index sequence (e.g., short oligonucleotide sequences to uniquely tag each molecule in a sample library, and/or to tag every molecule in one library with a sequence that is distinct from sequences used to tag molecules of anther library, alternatively referred to as a sample barcode), and a sequencing primer (SP) site, as illustrated in FIGS. 2A-2B. In embodiments, the adapters further include a platform priming capture (ppC) sequence, as illustrated in FIGS. 2C-2D. The ppC sequences are designed to have a low probability of unintended interactions with other adapters and immobilized oligonucleotides. Additionally, in embodiments, the 5' end of the surface immobilized ppC sequences is phosphorylated for efficient ligation and circularization. In embodiments, the pp1 sequence includes 5'-AATGATACGGCGACCACCG (SEQ ID NO:5) (P5) or the complement thereof. In embodiments the pp2 sequence includes 5'-CAAGCAGAAGACGGCATACGA (SEQ ID NO:6) (P7), or the complement thereof. Typically, the sequencing primer in P1 is different than the sequencing primer in P2. For clarity, FIGS. 2A-2B shows embodiments of the P1 and P2 sequences and not the complements thereof, as one having ordinary skill in the art would understand that P1' refers to the complement of P1. For example, when the P1 adapter comprises (pp1)-(i)-(SP1), the complement thereof is (SP1')-(i')-(pp1') (in 5' to 3' orientation). The index sequence in P1 may be the same or different to the index sequence in P2.

To circularize the ss template DNA, the target ssDNA is brought into contact with a substrate containing an immobilized splint primer (i.e., 5'-linker-P2-P1'), as illustrated in FIG. 1B. Generally, to form a cluster of monoclonal amplicons a plurality of immobilized splint primers are present on the surface, however for clarity only one splint primer is shown. The immobilized splint primer includes a nucleic acid sequence complementary to the 5'-adapter and the 3'-adapter of the target ssDNA, which is depicted as P2 and P1' in FIG. 1B due to the ssDNA having a P2' and a P1 adapter. The length of this complementary region needs to be sufficiently large to efficiently hybridize both ends of the target DNA.

Figure 1E:
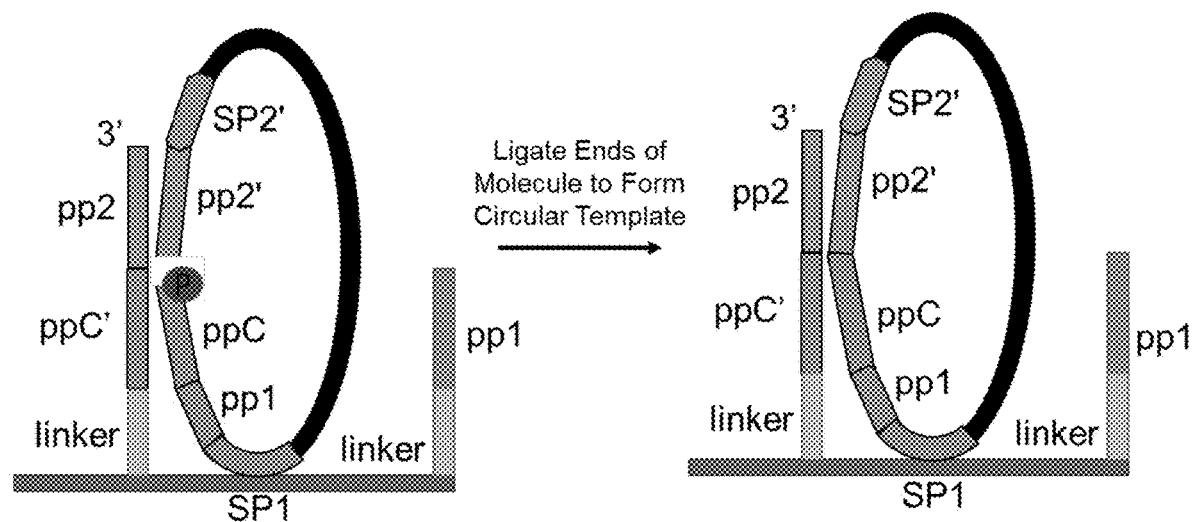
Figure 1F:
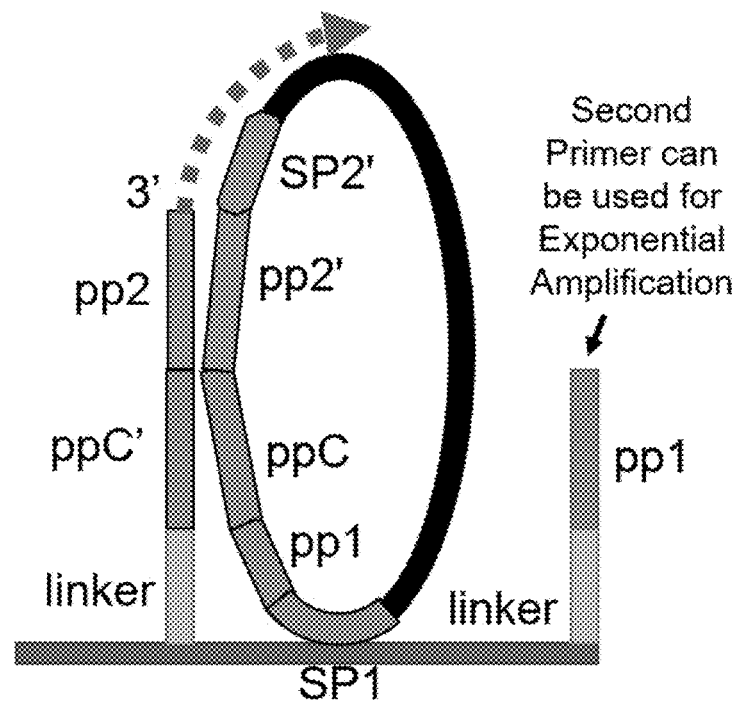

The ssDNA hybridizes to the immobilized splint primer, i.e., P2' of the primed template hybridizes with P2 region of the immobilized splint primer, and P1 hybridizes with the P1' region of the immobilized splint primer, see for example FIG. 1B and FIG. 1E. The 5' end and the 3' end of the hybridized primed template are ligated together (e.g., using AmpLigase®) thus forming a circularized ssDNA. The circularized ssDNA is then subjected to rolling circle amplification methods (FIG. 1C or FIG. 1F) to produce a long continuous single-stranded product (i.e., a concatemer). A second oligo can also be attached to the surface that is complementary to at least a portion of the complement of one of the adapters of the target ssDNA. This second oligo may be referred to as an exponential amplification primer and may include a portion of the adapter sequence or an identical adapter sequence. For example, as depicted in FIG. 1E, the exponential amplification primer is pp1, which is identical to a region of the P1 adapter of the ssDNA. The presence of the exponential amplification primer serves to facilitate exponential amplification of the RCA product either though exponential RCA or through bridge PCR after an initial RCA. For example, the exponential amplification primer may hybridize and amplify a portion of the rolled product to exponentially amplify the target ssDNA.

Figure 3:
FIG. 3 shows embodiments of splint primer sequences and truncated variants thereof, shown with the optional poly-T linker on the 5' ends of the primer sequences. The sequences are as follows, from 5' to 3': splint primer P1'P2 5'-TTTTTTTTTTTCCCCTTGCGCCGCATTAT-TGCAGCA AAACAGGGGTATCGA*T (SEQ ID NO:1); truncated splint primer 13 P1' 5'-TTTTTTTTTTCCGCCG-CATTATT GCAGCAAAACAGGGGTATCGA*T (SEQ ID NO:2), referred to as TS-13P1'; truncated splint primer 9 P1' 5'-TTTTTTTTTTCGCATTATT GCAGCAAAACAGGGGTATCGA*T (SEQ ID NO:3), referred to as TS-9P1'; truncated splint primer 6 P1' 5'-TTTTTTTTTTATTATTGCAGCAAAACAGGGGTATC GA*T (SEQ ID NO:4), referred to as TS-6P1'.

Ideally, complementarity between the exponential amplification primer and immobilized splint primer should be minimized to reduce primer-primer interactions. This can be achieved by targeting different portions of the template-associated adapter. For example, to limit interaction with a surface immobilized exponential amplification primer P1, a truncated splint primer with P2 and (P1-T)', where (P1-T) is the complement of the P1 adapter wherein the platform primer 1 sequence contains a portion of the complementary P1 sequence (e.g., 13, 9, or 6 nucleotides of P1'). For example, FIG. 3 depicts splint primers and truncated variants thereof. Alternatively, the splint primer can consist of the P2 sequence and a portion of P1' sequence, and the exponential amplification primer could be either all of the P1 primer sequence or a region of the P1 primer that does not overlap with P1 primer sequence targeted by the splint primer (FIG. 1E). Alternatively, this could be achieved by using a splint primer consisting of the P1' and P2 primer sequence and the exponential amplification primer is the SP1 (sequencing primer) sequence. In embodiments, the surface immobilized sequences have no complementarity to each other, for example as depicted in FIG. 1E.

The 5' end of any of the surface immobilized linkers may be covalently attached to a solid surface via an optional linker. The linker tethering the surface immobilized splint primer and the optional exponential amplification primer may be any linker capable of localizing nucleic acids to arrays. The linkers may be the same, or the linkers may be different. Solid-supported molecular arrays have been generated previously in a variety of ways, for example the attachment of biomolecules (e.g., proteins and nucleic acids) to a variety of substrates (e.g., glass, plastics, or metals) underpins modem microarray and biosensor technologies employed for genotyping, gene expression analysis and biological detection. Silica-based substrates are often employed as supports on which molecular arrays are constructed, and functionalized silanes are commonly used to modify glass to permit a click-chemistry enabled linker to tether the biomolecule.

It is beneficial to increase the linker-length, therefore the linkers may also include spacer nucleotides. Including spacer nucleotides in the linker puts the polynucleotide (e.g. splint primer) in an environment having a greater resemblance to free solution. This can be beneficial, for example, in enzyme-mediated reactions such as sequencing by synthesis. It is believed that such reactions suffer less steric hindrance issues that can occur when the polynucleotide is directly attached to the solid support or is attached through a very short linker (e.g., a linker comprising about 1 to 3 carbon atoms). Spacer nucleotides form part of the polynucleotide but do not participate in any reaction carried out on or with the polynucleotide (e.g. a hybridization or amplification reaction). In embodiments, the spacer nucleotides include 1 to 20 nucleotides. In embodiments, the linker includes 10 spacer nucleotides. It is preferred to use polyT spacers, although other nucleotides and combinations thereof can be used. In embodiments, the linker includes 10 T spacer nucleotides. Spacer nucleotides are typically included at the 5' ends of polynucleotides which are attached to a suitable support. Attachment can be achieved via a phosphorothioate present at the 5' end of the polynucleotide. The linker may be a carbon-containing chain such as those of formula $-(CH_2)n-$ wherein "n" is from 1 to about 1000. However, a variety of other linkers may be used so long as the linkers are stable under conditions used in DNA sequencing. In embodiments, the linker includes polyethylene glycol (PEG) having a general formula of $-(CH_2-CH_2-O)m-$, wherein m is from about 1 to 500. In embodiments, m is 8 to 24. In embodiments, m is 10 to 12.

As mentioned above, the linkers may be the same, or the linkers may be different. The linker for the splint primer may be a different composition or a different length than the linker for the exponential amplification primer.

Surface-Conjugation of Splint Oligo to Generate Monoclonal Colonies: A plurality of splint primers complementary to the 5' and 3' ends of a single-stranded target molecule were chemically attached to polymer-coated glass slide through DBCO-azide click chemistry. This glass slide was assembled into a flow cell prior to splint primer deposition.

Hybridization of Target Sequence: An amplified pool of a single DNA target molecule with a 5' phosphate group was resuspended in a DNA hybridization buffer, heated to 95° C. to denature into single-stranded DNA, cooled and added to the flow cell described above. This flow cell was pre-heated to 65° C. for hybridization of the target DNA to the surface immobilized splint primers. The flow cell was then gradually cooled to 45° C. and further incubated at 45° C. (total hybridization time 30 minutes).

Ligation of Target Sequence: The templates hybridized to the splint primers were ligated by adding DNA Ligase (Ampligase®) for 30 minutes at 45° C.

DNA Amplification by RCA: The ligated circle was then amplified by rolling circle amplification (RCA) where the surface-immobilized splint oligo was used as the primer, and the ligated target sequence was the template. RCA was performed according to known techniques in the art, e.g., by adding Phi29 and dNTPs and incubating at 37° C. for 60 minutes. The resulting clusters were visualized by staining the amplified product with SYBR-Gold and visualized using fluorescent microscopy. To establish that ligation of linear templates was necessary to get amplification by this method, experiments were done in the presence and absence of DNA Ligase; see FIG. 4A. Clusters were formed only in those conditions that contained DNA ligase demonstrating the feasibility of this approach for NGS cluster formation.

Example 2. Ligating a Complex Library on a Surface

Figure 5:
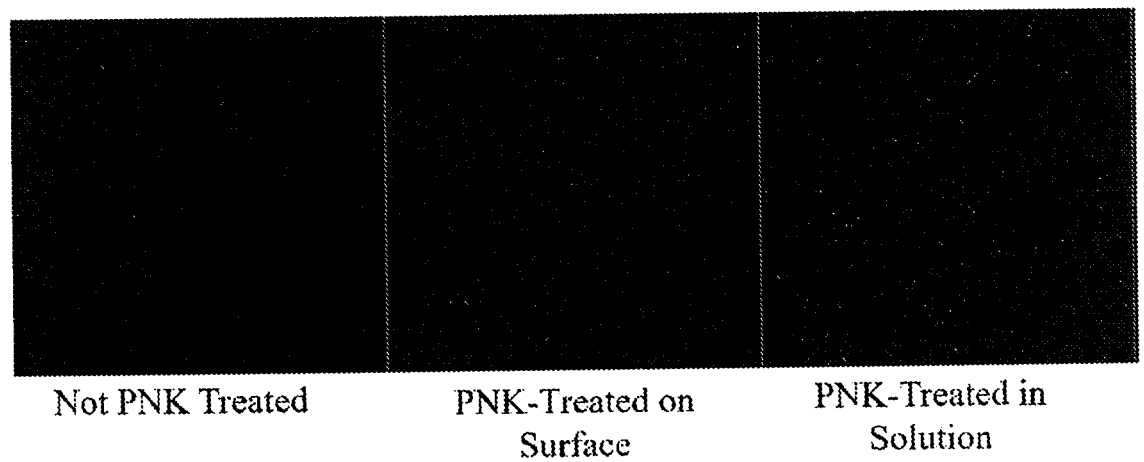
FIG. 5. Linear molecules can be directly phosphorylated on-surface prior to circularization. Fluorescent microscopy images of RCA-amplified product on surface. A library comprised of a complex mixture of inserts was prepared according to standard protocols and circularized on surface and clustered by RCA. Clusters were stained with Sybr-Gold and are colored green. Red dots are focusing beads added for visualization. The library prior to circularization on surface was either un-phosphorylated (left image, not treated with T4 PNK phosphorylation), phosphorylated on surface (center image), or phosphorylated in solution (right image, T4 PNK phosphorylation in solution).

Typical NGS-libraries are not composed of a single template type, but rather a complex mixture of templates. To determine if a standard sequencing library could be circularized and clustered by this method, a library was prepared according to Twist Biosciences NGS library prep kit protocols producing a library of unphosphorylated templates. Two methods for phosphorylating the 5' ends were tested: phosphorylation was performed in solution prior to hybridization, or on-surface after hybridization. For both methods, phosphorylation was performed by incubating the library with a T4 Polynucleotide Kinase (PNK) for 30 minutes at 37° C. Libraries may be phosphorylated and circularized by either method to produce monoclonal clusters, as shown in FIG. 5.

Example 3. Varying the Ratio of Splint Primers/Exponential Amplification Primers The relative concentration of splint primers and exponential amplification primers affects the cluster size and density. Splint primers (P1'P2) and blocked exponential amplification primers (P1) were chemically attached to a polymer-coated glass slide at different concentrations (see Table 1). This polymer-coated glass slide was assembled into a flow cell prior to primer deposition. The P1 primers were blocked with P1'-oligo during the initial deposition to limit interactions with the splint primer. The blocking oligo was removed with 0.1M NaOH prior to seeding with a plurality of template ssDNA molecules. The hybridized ssDNA molecules were circularized with AmpLigase® according to standard reaction protocols (e.g., 1×AmpLigase® Buffer for 30 minutes at 45° C.). The circularized molecules were amplified with a mutant phi29 polymerase for 1 hour at 37° C. in an amplification buffer with nucleotides to produce forward and reverse products. The resulting clusters were visualized by staining the clusters with SYBR-Gold and visualized using fluorescent microscopy.

TABLE 1

Ratios of surface immobilized oligos.

| P1 concentration (µM) | Splint primer (P1'/P2) concentration (µM) | Ratio [P1]:[P1'/P2] |
|---|---|---|
| 0.05 | 0.10 | 0.5 |
| 0.10 | 0.10 | 1.0 |
| 0.20 | 0.10 | 2.0 |

Analyzing the resulting clusters and their intensities suggests that higher concentrations of P1 on the surface allows for more reverse product to form as determined from the relative increase in cluster intensity. As the concentration of P1 increases, however, there is a decrease in overall feature counts within the cluster (i.e., a decrease in ssDNA hybridization events) likely due to competitive P1/splint interactions reducing the available splint primers for hybridization.

Example 4. Ligation of *Salmonella* Genome onto a Surface

Utilizing the methods described herein, various lengths of the pp1 primer sequence were interrogated to determine (a) if the pp1 sequence is critical to achieve on-surface ligation, and (b) the length of the pp1 sequence effects on ligation efficiency. A 12-lane flow cell was prepared following the steps below.

TABLE 2

The desired surface primer, template, and on-surface ligation conditions for each lane are detailed herein.

| Lane | Surface immobilized oligos | | Template | Ligation (37° C. for 30 min) |
|---|---|---|---|---|
| 1 | 2.0 µM P1 | 2.0 µM P1'P2 (15 nt pp1) | 3 pM Salm P1 (15 nt pp1') SSC | 4 U/µl T4 |
| 2 | 2.0 µM P1 | 2.0 µM P1'P2 (15 nt pp1) | 3 pM Salm P1 (15 nt pp1') linear | 4 U/µl T4 |
| 3 | 2.0 µM P1 | 2.0 µM P1'P2 (20 nt pp1) | 3 pM Salm P1 (20 nt pp1') SSC | 4 U/µl T4 |
| 4 | 2.0 µM P1 | 2.0 µM P1'P2 (20 nt pp1) | 3 pM Salm P1 (20 nt pp1') | 4 U/µl T4 |
| 5 | 2.0 µM P1 | 2.0 µM P1'P2 (15 nt pp1) | 3 pM Salm P1 (15 nt pp1') SSC | 4 U/µl T4 |
| 6 | 2.0 µM P1 | 2.0 µM P1'P2 (15 nt pp1) | 3 pM Salm P1 (15 nt pp1') linear | 4 U/µl T4 |
| 7 | 2.0 µM P1 | 2.0 µM P1'P2 (10 nt pp1) | 3 pM Salm P1 (10 nt pp1') linear | 4 U/µl T4 |
| 8 | 2.0 µM P1 | 2.0 µM P1'P2 (10 nt pp1) | 3 pM Salm P1 (10 nt pp1') SSC | 4 U/µl T4 |
| 9 | 2.0 µM P1 | 2.0 µM P1'P2 (15 nt pp1) | 3 pM Salm P1 (15 nt pp1') linear | No Ligase |
| 10 | 2.0 µM P1 | 2.0 µM P1'P2 (no pp1) | 3 pM Salm P1 (15 nt pp1') linear | 4 U/µl T4 |
| 11 | 2.0 µM P1 | 2.0 µM P1'P2 (15 nt pp1) | 3 pM Salm P1 linear (no pp1') | 4 U/µl T4 |
| 12 | 2.0 µM P1 | 2.0 µM P1'P2 (15 nt pp1) | No Template | 4 U/µl T4 |

Each linear *Salmonella* template splint length (20-, 15-, or 10 nt pp1) was compared to its corresponding single-stranded circular (SSC) template (lanes 3-8). A 15 nt pp1P1 sequence was used as a positive control (lanes 1-2). Splint annealing negative controls consisted of a pp1'P1 template paired with standard P1'P2 (no pp1) surface primers (lane 10) and a standard P1 linear template paired with pp1 surface primers (lane 11). Additional negative controls included a no ligase sample (lane 9) and a no template control (lane 12).

Surface-Conjugation of Splint Oligo: A plurality of splint primers (P1'P2 surface primer) complementary to the 5' and 3' ends of a single-stranded target molecule were chemically attached to polymer-coated glass slide through DBCO-azide click chemistry. This polymer-coated glass slide was assembled into a flow cell prior to primer deposition.

QC of Surface Primer Conjugation: The monoclonal clusters can proceed to any necessary post-processing steps such as blocking of free 3' ends, removal of select amplicons, or hybridization of a sequencing primer. The clusters were quantified by introducing a nucleic acid stain (e.g., SYBR® Gold stain available from Thermo Fisher, Catalog #S11494 or a FAM (6-fluorescein amidite) labeled oligonucleotide) in the presence of a buffer, and allowed to incubate with the amplicons for 10 minutes. After a wash, the substrate containing the stained amplicons was imaged and subjected to post-processing analysis to determine cluster size and brightness. After these steps, clusters were ready for sequencing.

For example, successful surface primer conjugation was confirmed by hybridizing either P1-Cy5 or P2'-Cy5 probes and performing fluorescent microscopy. The intensity of Cy5 probe was proportional to amount of surface primer conjugated. Following QC, Cy5 probes are removed with freshly diluted 0.1M NaOH, washed, and visualized by fluorescent microscopy to confirm successful probe removal.

Template Hybridization: An amplified pool of DNA target molecules containing a pp1' P1 hybridization region with a 5' phosphate group was resuspended in a DNA hybridization buffer containing an additive (e.g., 30% ethylene glycol). Template DNA was applied to flow cell. The flow cell was heated to 85° C. for 5 minutes to denature into single-stranded DNA. The flow cell was then gradually cooled from 85° C. to 45° C. and further incubated at 45° C. (total hybridization time 30 minutes). Following incubation, the flow cell was washed.

Ligation of Target Sequence: T4 DNA Ligase in ligase reaction buffer was applied to the flow cell and incubated for 30 minutes at 37° C. Ligase reaction was stopped by adding Tris buffer with high EDTA and incubating for 1 minute. The flow cell was then washed prior to amplification.

DNA Amplification by RCA: The ligated circle was then amplified by rolling circle amplification (RCA) where the surface-immobilized splint oligo was used as the primer, and the ligated target sequence was the template. These templates were suitable for sequencing as described herein (e.g., Example 5). Alternatively, further amplification methods, such as bridge amplification, were carried out on these templates.

Additional DNA Amplification by Thermal Bridge PCR: Following RCA, thermal bridge PCR (t-bPCR) amplification solution was applied to the lanes followed by a standard thermal cycling protocols known in the art, including thermally cycling between 85° C. denaturing cycles and 60° C. annealing cycles to further amplify the templates. The templates may then proceed to additional post-processing techniques, such cleaving of particular surface primer populations, blocking of free 3' OH, hybridization of sequencing primers, and cluster quality measurements.

Figure 4A:
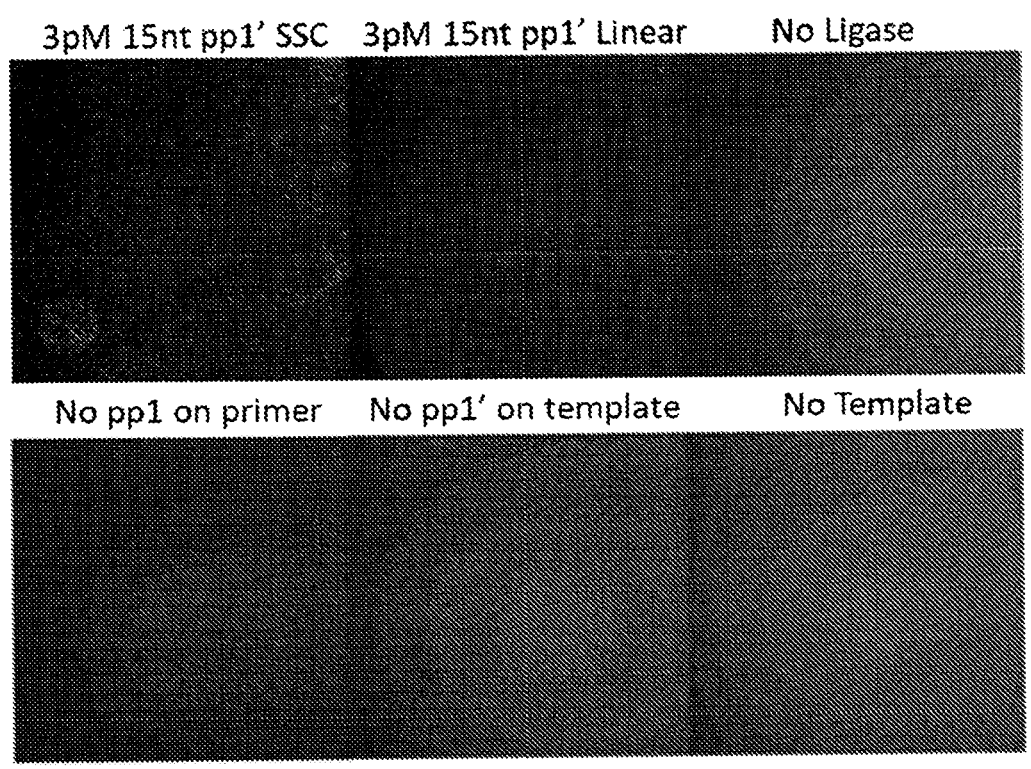
FIGS. 4A-4B. Linear template can be circularized and amplified on surface. Fluorescent microscopy images of RCA-amplified product on surface. An initial template was circularized on the surface (linear) and amplified according to amplification methods described herein or circularized in solution (SSC) and amplified.

We found that the presence of the combination of both pp1 and pp1' was needed for efficient on-surface template circularization, for example see the top leftmost and middle image of FIG. 4A. The platform primers pp1 or pp1' alone did not result in ligation and subsequent amplification, see the bottom leftmost and middle image of FIG. 4A.

Figure 4B:
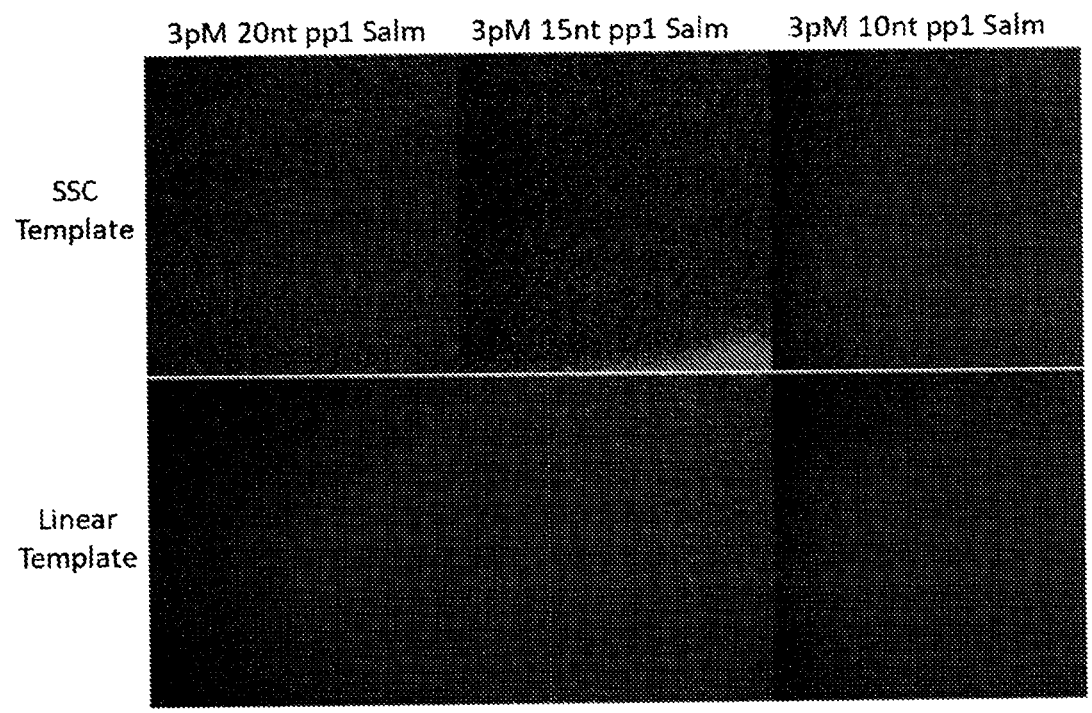

The overall length of the immobilized primer also has an effect on the efficiency of ligation, and ultimately on the amount of sequenceable clusters. While clusters formed in all conditions tested, as presented in FIG. 4B, the low and medium ranged length (10 nt and 15 nt) primers resulted in significantly more sequenceable clusters compared to the longer length (20 nt) primers. This experiment was repeated varying the length of the ppC sequence. All lengths examined, 10 nt, 15 nt, and 20 nt sequences were all successful at producing sequenceable clusters.

Example 5. Sequencing Surface-Ligated Template

We compared templates prepared according to the methods described herein, e.g., within Example 4, to templates ligated during standard library preparation protocols in solution. A flow cell was prepared according to the conditions outlined in Table 3. A pre-circularized DNA library, P1 *Salmonella* SSC template with a 10 nt pp1'-P1 *Salmonella* SSC template was compared to a 10 nt pp1'-P1 *Salmonella* linear template that was used for the on-surface ligation.

TABLE 3

| Conditions for sequencing. | | |
|---|---|---|
| Primer | Template | Ligation |
| 2.0 µM P1 | 2.0 µM P1'P2 (10 nt pp1) | 1.5 pM P1 (10 nt pp1') *Salmonella* pre-circularized | None |
| 2.0 µM P1 | 2.0 µM P1'P2 (10 nt pp1) | 1.5 pM P1 (10 nt pp1') *Salmonella* linear | 4 U/µl T4 37° C. for 30 m |

Additional post-amplification processing steps were performed prior to sequencing, including adding focusing beads and neutralizing reactive moieties on the polymer surface, prior to sequencing primer hybridization.

Sequencing Primer Hybridization: The lanes were aspirated and filled with 2× flow channel volume of sequencing primer (as indicated in Table 3). The flow cell was then incubated at 65° C. for 15 minutes. The flow cell was then washed by flowing 10× flow channel volume of Wash Buffer.

Figure 6:
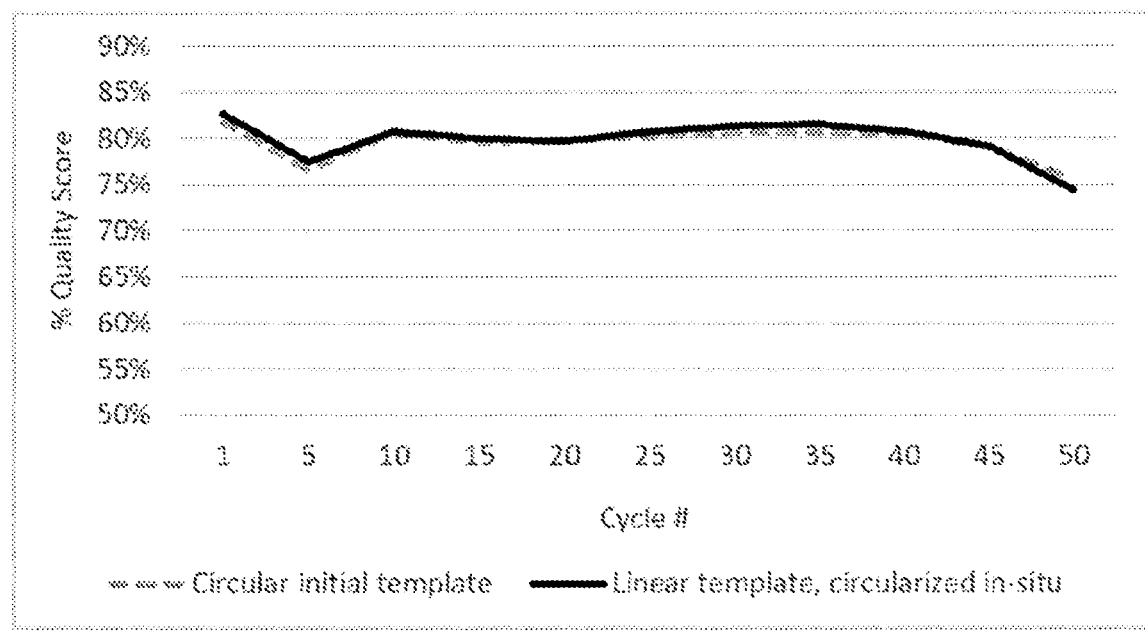
FIG. 6. Results from a sequencing experiment sequencing a template for 50 cycles comparing standard template ligation (i.e., in solution) to the on-surface ligation and amplification methods described herein.

Results: Sequencing for 50 cycles revealed no apparent difference between the templates ligated on-surface compared to the templates ligated during library preparation; see for example the quality scores presented in FIG. 6 comparing the pp1' linear to pp1' circle. The quality score reported in FIG. 6 show no significant differences in quality scores for templates that were circularized in-situ compared to standard solution-phase circularization techniques, further revealing the circularization method described herein provides greater amplification workflow efficiency without a need for the purification step or exonuclease treatment and without sacrificing sequencing quality.

P-Embodiments

The present disclosure provides the following illustrative embodiments.

Embodiment P1. A method of sequencing a linear template polynucleotide, the method comprising: (a) hybridizing the linear template polynucleotide to a splint primer immobilized on a surface, wherein (i) the splint primer comprises, in the 5' to 3' direction, a first sequence and a second sequence, (ii) the first sequence is complementary to a 5' portion of the linear template polynucleotide, and (iii) the second sequence is complementary to a 3' portion of the linear template polynucleotide; (b) circularizing the linear template polynucleotide to form a circular template polynucleotide comprising a continuous strand lacking free 5' and 3' ends; (c) amplifying the circular template polynucleotide by extending the splint primer with a strand-displacing polymerase, wherein the extension generates a first extension product comprising one or more complements of the circular template polynucleotide; (d) hybridizing the first extension product to one or more surface-immobilized oligonucleotides immobilized on the surface; and (e) sequencing the first extension product or a complement thereof by extending a sequencing primer hybridized thereto.

Embodiment P2. The method of Embodiment P1, wherein the linear template polynucleotide is generated by joining a first adapter polynucleotide to a 5' end of a sample polynucleotide, and joining a second adapter polynucleotide to a 3' end of the sample polynucleotide, wherein (i) the first adapter polynucleotide comprises a portion that hybridizes to the first sequence of the splint primer, and (ii) the second adapter polynucleotide comprises a portion that hybridizes to the second sequence of the splint primer.

Embodiment P3. The method of Embodiment P2, wherein one or both of the first adapter polynucleotide and the second adapter polynucleotide comprise a portion that does not hybridize to the splint primer, wherein after joining to the sample polynucleotide, the portion that hybridizes to the splint primer is distal to the portion that does not hybridize to the splint primer.

Embodiment P4. The method of Embodiment P3, wherein the portion of the first adapter polynucleotide that does not hybridize to the splint primer, the portion of the second adapter polynucleotide that does not hybridize to the splint primer, or both comprises an index sequence.

Embodiment P5. The method of Embodiment P3 or Embodiment P4, wherein the portion that does not hybridize to the splint primer comprises a sequencing primer binding sequence.

Embodiment P6. The method of any one of Embodiment P1-Embodiment P5, wherein the first extension product comprises a plurality of complements of the circular template polynucleotide.

Embodiment P7. The method of Embodiment P6, wherein the one or more surface-immobilized oligonucleotides comprise a plurality of the surface-immobilized oligonucleotides.

Embodiment P8. The method of any one of Embodiment P1-Embodiment P7, wherein circularizing the linear template polynucleotide comprises joining the 5' end of the linear template polynucleotide directly to the 3' end of the linear template polynucleotide.

Embodiment P9. The method of any one of Embodiment P1-Embodiment P7, wherein circularizing the linear template polynucleotide comprises extending the 3' end of the linear template polynucleotide and joining the extended 3' end to the 5' end of the linear template polynucleotide.

Embodiment P10. The method of any one of Embodiment P1-Embodiment P9, wherein circularizing comprises a ligation reaction.

Embodiment P11. The method of any one of Embodiment P1-Embodiment P10, wherein amplifying the circular template polynucleotide comprises incubating the template polynucleotide with the strand-displacing polymerase (a) for about 1 minute to about 2 hours, and/or (b) at a temperature of about 20° C. to about 50° C.

Embodiment P12. The method of any one of Embodiment P1-Embodiment P11, wherein the strand-displacing polymerase is a phi29 polymerase, a phi29 mutant polymerase, or a thermostable phi29 mutant polymerase.

Embodiment P13. The method of any one of Embodiment P2-Embodiment P12, wherein the one or more surface-immobilized oligonucleotides hybridize to a complement of: (a) the portion of the first adapter polynucleotide that hybridizes to the first sequence of the splint primer; or (b) the portion of the second adapter polynucleotide that hybridizes to the second sequence of the splint primer.

Embodiment P14. The method of any one of Embodiment P3-Embodiment P12, wherein the one or more surface-immobilized oligonucleotides hybridize to a complement of: (a) the portion of the first adapter polynucleotide that does not hybridize to the splint primer; or (b) the portion of the second adapter polynucleotide that does not hybridize to the splint primer.

Embodiment P15. The method of any one of Embodiment P1-Embodiment P14, wherein the one or more surface-immobilized oligonucleotides comprise blocking groups at their 3' ends that prevent polymerase extension.

Embodiment P16. The method of any one of Embodiment P1-Embodiment P15, wherein the method does not comprise extending the one or more surface-immobilized oligonucleotides.

Embodiment P17. The method of any one of Embodiment P1-Embodiment P14, further comprising extending the one or more surface-immobilized oligonucleotides hybridized to the first extension product with a polymerase.

Embodiment P18. The method of Embodiment P15, further comprising removing the blocking groups and extending the surface-immobilized oligonucleotides hybridized to the first extension product with a polymerase.

Embodiment P19. The method of any one of Embodiment P2-Embodiment P18, wherein the sequencing primer hybridizes to a complement of: (a) the portion of the first adapter polynucleotide that hybridizes to the first sequence of the splint primer; or (b) the portion of the second adapter polynucleotide that hybridizes to the second sequence of the splint primer.

Embodiment P20. The method of any one of Embodiment P3-Embodiment P18, wherein the sequencing primer hybridizes to a complement of: (a) the portion of the first adapter polynucleotide that does not hybridize to the splint primer; or (b) the portion of the second adapter polynucleotide that does not hybridize to the splint primer.

Embodiment P21. The method of any one of Embodiment P1-Embodiment P20, wherein the splint primer is about 5 to about 25 nucleotides in length.

Embodiment P22. The method of any one of Embodiment P1-Embodiment P21, wherein the circular template polynucleotide is about 100 to about 1000 nucleotides in length.

Embodiment P23. A substrate comprising: (a) a splint primer immobilized on the substrate via a first linker; (b) a plurality of surface-immobilized oligonucleotides immobilized to the substrate via a second linker; and (c) a linear template polynucleotide hybridized to the splint primer; wherein (i) the splint primer comprises, in the 5' to 3' direction, a first sequence and a second sequence, (ii) the first sequence is complementary to a 5' portion of the linear template polynucleotide, (iii) the second sequence is complementary to a 3' portion of the linear template polynucleotide, and (iv) the plurality of surface-immobilized oligonucleotides are hybridizable to a complement of the linear template polynucleotide.

Embodiment P24. The substrate of Embodiment P23, wherein the linear template polynucleotide comprises a first adapter polynucleotide joined to a 5' end of a sample polynucleotide, and a second adapter polynucleotide joined to a 3' end of the sample polynucleotide, wherein (i) the first adapter polynucleotide comprises a portion that is hybridized to the first sequence of the splint primer, and (ii) the second adapter polynucleotide comprises a portion that is hybridized to the second sequence of the splint primer.

Embodiment P25. The substrate of Embodiment P24, wherein one or both of the first adapter polynucleotide and the second adapter polynucleotide comprise a portion that is not hybridized to the splint primer, wherein the portion that is hybridized to the splint primer is distal to the portion that is not hybridized to the splint primer.

Embodiment P26. The substrate of Embodiment P25, wherein the portion that is not hybridized to the splint primer comprises an index sequence.

Embodiment P27. The substrate of any one of Embodiment P24-Embodiment P26, wherein the plurality of surface-immobilized oligonucleotides are hybridizable to a complement of: (a) the portion of the first adapter polynucleotide that is hybridized to the first sequence of the splint primer; or (b) the portion of the second adapter polynucleotide that is hybridized to the second sequence of the splint primer.

Embodiment P28. The substrate of any one of Embodiment P25-Embodiment P26, wherein the plurality of surface-immobilized oligonucleotides are hybridizable to a complement of: (a) the portion of the first adapter polynucleotide that is not hybridized to the splint primer; or (b) the portion of the second adapter polynucleotide that is not hybridized to the splint primer.

Embodiment P29. The substrate of any one of Embodiment P23-Embodiment P28, wherein the plurality of surface-immobilized oligonucleotides comprise blocking groups at their 3' ends that prevent polymerase extension.

Embodiment P30. The substrate of any one of Embodiment P23-Embodiment P29, wherein the splint primer is about 5 to about 25 nucleotides in length.

Embodiment P31. The substrate of any one of Embodiment P23-Embodiment P30, wherein the linear template polynucleotide is about 100 to about 1000 nucleotides in length.

What is claimed is:

1. A method of amplifying a single-stranded polynucleotide, the method comprising:
   contacting a solid support with the single-stranded polynucleotide comprising a first primer binding sequence and a second primer binding sequence, and hybridizing said first primer binding sequence and said second primer binding sequence to a splint oligonucleotide attached to the solid support;
   extending the first primer binding sequence and ligating the extended first primer binding sequence to the second primer binding sequence together to form a circular polynucleotide;
   extending the splint oligonucleotide with a polymerase to generate an amplification product comprising a complement of the circular polynucleotide; and
   hybridizing the amplification product to a second oligonucleotide attached to the solid support comprising a blocking group at a 3' end that prevents polymerase extension.

2. The method of claim 1, wherein said second oligonucleotide comprises the second primer binding sequence.

3. The method of claim 1, wherein said single-stranded polynucleotide comprises a third primer binding sequence, and said second oligonucleotide comprises said third primer binding sequence.

4. The method of claim 1, wherein said solid support is a bead or substantially planar.

5. The method of claim 1, wherein said amplification product comprises a plurality of complements of the circular polynucleotide.

6. The method of claim 1, wherein extending comprises incubating the splint oligonucleotide with a strand-displacing polymerase (a) for about 1 minute to about 2 hours, and/or (b) at a temperature of about 20° C. to about 50° C.

7. The method of claim 6, wherein said strand-displacing polymerase is a phi29 polymerase, a phi29 mutant polymerase, or a thermostable phi29 mutant polymerase.

8. The method of claim 1, wherein the circular polynucleotide is about 100 to about 1000 nucleotides or about 1000 to about 5000 nucleotides in length.

9. The method of claim 1, wherein said amplification product comprises one or more cleavable sites.

10. The method of claim 1, wherein said solid support comprises an array of wells.

11. The method of claim 1, wherein said solid support comprises a plurality of splint oligonucleotides randomly distributed on the solid support.

12. The method of claim 1, further comprising sequencing the amplification product.

13. The method of claim 1, wherein said solid support comprises a polymer, wherein said splint oligonucleotide and second oligonucleotide are covalently attached to said polymer.

14. A method of forming a plurality of tethered amplification products on a solid support, said method comprising:
   contacting a solid support with a sample comprising a plurality of single-stranded polynucleotides
   hybridizing a first primer binding sequence and a second primer binding sequence of a single-stranded polynucleotide of said plurality of single-stranded polynucleotides to a splint oligonucleotide attached to the solid support, wherein said splint oligonucleotide comprises, from 5' to 3', a first primer sequence, a third sequence, and a second primer sequence, and;
   extending the first primer binding sequence to form a complement of the third sequence and ligating the complement of the third sequence and the second primer binding sequence together to form a circular polynucleotide;
   extending the splint oligonucleotide with a polymerase to generate an amplification product comprising a complement of the circular polynucleotide; and hybridizing the amplification product to a second oligonucleotide attached to the solid support, wherein said second oligonucleotide is attached to the solid support at a 5'-end and comprises a blocking group at a 3' end that prevents polymerase extension, thereby forming a plurality of tethered amplification products.

15. The method of claim 14, wherein said solid support comprises a plurality of second oligonucleotides.

16. The method of claim 14, wherein said solid support comprises an array of wells.

17. The method of claim 14, wherein said solid support comprises a plurality of splint oligonucleotides randomly distributed on the solid support.

18. The method of claim 14, wherein said solid support comprises a patterned surface.

19. The method of claim 14, further comprising sequencing said tethered amplification products on said solid support.

20. The method of claim 19, wherein sequencing comprises hybridizing one or more sequencing primers to the tethered amplification products and generating one or more sequencing reads by detecting a sequence of signals.

21. The method of claim 1, wherein the splint oligonucleotide includes a first sequence complementary to a first primer sequence, a second primer sequence, and a third primer sequence, wherein the third primer sequence is between the first and the second primer sequence.

22. The method of claim 21, wherein the third primer sequence is a sequencing primer binding sequence.

23. A method of amplifying a single-stranded polynucleotide, the method comprising:
   contacting a solid support with the single-stranded polynucleotide comprising a first primer binding sequence and a second primer binding sequence, and hybridizing said first primer binding sequence and said second primer binding sequence to a splint oligonucleotide attached to the solid support;

ligating the first primer binding sequence and a second primer binding sequence together to form a circular polynucleotide;

extending the splint oligonucleotide with a polymerase to generate an amplification product comprising a complement of the circular polynucleotide; and hybridizing the amplification product to a second oligonucleotide comprising a blocking group at a 3' end that prevents polymerase extension, wherein said second oligonucleotide is attached to the solid support.

* * * * *

```
                        SEQUENCE LISTING

Sequence total quantity: 6
SEQ ID NO: 1            moltype = DNA  length = 52
FEATURE                 Location/Qualifiers
misc_feature            1..52
                        note = Synthetic construct
misc_feature            1..52
                        note = Splint primer P1'P2 referred to as TS-13P1'
misc_feature            52
                        note = Poly-T linker may be present or absent
source                  1..52
                        mol_type = other DNA
                        organism = synthetic construct
SEQUENCE: 1
tttttttttt tccccttgcg ccgcattatt gcagcaaaac aggggtatcg at            52

SEQ ID NO: 2            moltype = DNA  length = 45
FEATURE                 Location/Qualifiers
misc_feature            1..45
                        note = Synthetic construct
misc_feature            1..45
                        note = Truncated splint primer 9 P1' referred to as TS-9P1'
misc_feature            45
                        note = Poly-T linker may be present or absent
source                  1..45
                        mol_type = other DNA
                        organism = synthetic construct
SEQUENCE: 2
tttttttttt ccgccgcatt attgcagcaa aacaggggta tcgat                    45

SEQ ID NO: 3            moltype = DNA  length = 41
FEATURE                 Location/Qualifiers
misc_feature            1..41
                        note = Synthetic construct
misc_feature            1..41
                        note = Truncated splint primer 9 P1' referred to as TS-9P1'
misc_feature            41
                        note = Poly-T linker may be present or absent
source                  1..41
                        mol_type = other DNA
                        organism = synthetic construct
SEQUENCE: 3
tttttttttt cgcattattg cagcaaaaca ggggtatcga t                        41

SEQ ID NO: 4            moltype = DNA  length = 38
FEATURE                 Location/Qualifiers
misc_feature            1..38
                        note = Synthetic construct
misc_feature            1..38
                        note = Truncated splint primer 6 P1' referred to as TS-6P1'
misc_feature            38
                        note = Poly-T linker may be present or absent
source                  1..38
                        mol_type = other DNA
                        organism = synthetic construct
SEQUENCE: 4
tttttttttt attattgcag caaaacaggg gtatcgat                            38

SEQ ID NO: 5            moltype = DNA  length = 19
FEATURE                 Location/Qualifiers
misc_feature            1..19
                        note = Synthetic construct
source                  1..19
                        mol_type = other DNA
                        organism = synthetic construct
```

```
SEQUENCE: 5
aatgatacgg cgaccaccg                                                    19

SEQ ID NO: 6           moltype = DNA  length = 21
FEATURE                Location/Qualifiers
misc_feature           1..21
                       note = Synthetic construct
source                 1..21
                       mol_type = other DNA
                       organism = synthetic construct
SEQUENCE: 6
caagcagaag acggcatacg a                                                 21
```